US005932426A

United States Patent [19]
Baralle et al.

[11] Patent Number: 5,932,426
[45] Date of Patent: Aug. 3, 1999

[54] MOLECULAR PRESENTING SYSTEM

[75] Inventors: Francesco Ernesto Baralle; Eduardo Scodeller; Sergio Tisminetzky, all of Trieste, Italy

[73] Assignee: International Centre For Genetic Engineering and Biotechnology Trieste, Italy

[21] Appl. No.: 08/776,585

[22] PCT Filed: Aug. 4, 1995

[86] PCT No.: PCT/EP95/03114

§ 371 Date: Mar. 31, 1997

§ 102(e) Date: Mar. 31, 1997

[87] PCT Pub. No.: WO96/05293

PCT Pub. Date: Feb. 22, 1996

[30] Foreign Application Priority Data

Aug. 8, 1994 [AU] Australia ................................ 1545/94

[51] Int. Cl.$^6$ .......................... G01N 33/53; C12P 21/00; C07K 16/00; C07H 21/04

[52] U.S. Cl. ....................... 435/7.2; 435/69.1; 435/320.1; 435/472; 530/300; 530/389.4; 536/23.72

[58] Field of Search ............................ 424/184.1, 192.1, 424/199.1; 435/6, 69.1, 94.4, 235.1, 320.1, 7.2, 472; 514/2; 536/23.4, 23.72; 530/300, 389.4

[56] References Cited

PUBLICATIONS

Cohen. Bumps on the vaccine road. Science. vol. 265:1371–1373, Sep. 2, 1994.

Greis et al. Site–specific glycosylation of the human cytomegalovirus tegument basic phosphoprotein (UL32) as serine 921 and serine 952. J. Virol. vol. 68(12):8339–8349, Nov. 18, 1994.

Kennard et al. The 25 amino acid residues at teh carboxy termius of the herpes simplex virus type 1 UL26.5 protein are required for the formation of the capsid shell around the scaffold. J. Gen. Virol. vol. 76:1611–1621, Jul. 11, 1995.

Sprent et al. Lymphocyte life–span and memory. Science. vol. 265:1395–1399, Sep. 2, 1994.

Ben–Yedida et al. Design of peptide and polypeptide vaccines. Curr. Opinion in Biotechnol. vol. 8:442–448, Aug. 4, 1997.

Fisher et al., "Crystallization of Viruslike Particles Assembled From Flock House Virus Coat Protein Expressed In A Baculovirus System", *Journal of Virology,* vol. 67(5):2950–2953, (1993).

Schneemann et al., "Use Of Recombinant Baculoviruses In Synthesis Of Morphologically Distinct Viruslike Particles Of Flock House Virus, A Nodavirus", *Journal of Virology,* vol. 67(5):2756–2763, (1993).

Rovinski et al., "Expression And Characterization Of Genetically Engineered Human Immunodeficiency Virus–Like Particles Containing Modified Envelope Glycoproteins: Implications For Development Of A Cross–Protective AIDS Vaccine", *Journal Of Virology,* vol. 66(7):4003–4012, (1992).

Wagner et al., "Induction Of Cytolytic T Lymphocytes Directed Towards The V3 Loop Of The Human of Immunodeficiency Virus Type 1 External Glycoprotein gp120 By $p55_{gag}$/V3 Chimeric Vaccinia Viruses", *Journal General Virology,* vol. 74:1261–1269, (1993).

Fisher et al., "Ordered Duplex RNA Controls Capsid Architecture In An Icosahedral Animal Virus", *Nature,* vol. 361:176–179, (1993).

Dasgupta et al., "Nucleotide Sequences Of Three Nodavirus RNA2's: The Messengers For Their Coat Protein Precursors", *Nucleic Acids Research,* vol. 17(18):7525–7526, (1989).

Tisminetzky et al., "Immunoreactivity of Chimeric Proteins Carrying the HIV–1 Epitope IGPGRAF Correlation Between Predicted Conformation And Antigenicity", *FEBS Letters,* vol. 353:1–4, (1994).

Scodeller et al., "A New Epitope Presenting System Displays a HIV–1 V3 Loop Sequence And Induces Neutralizing Antibodies", *Vaccine,* vol. 13(13):1233–1239, (1995).

*Primary Examiner*—James Ketter
*Assistant Examiner*—William Sandals
*Attorney, Agent, or Firm*—Foley & Lardner

[57] ABSTRACT

The invention refers to a molecular presentation system in which viral proteins are foreseen as carriers for heterologous amino acid sequences. Hereby, the viral protein is derived from small insect viruses, primarily from Flock House Virus (FHV), with a known 3-dimensional structure and amino acid sequence, whereby heterologous amino acid sequences, for example epitopes, are inserted in the outwardly directed loops of the viral capsid protein. Moreover, the expression of the FHV capsid protein in insect cells can produce mature virus like particles (VLP) through a recombinant baculovirus.

10 Claims, 36 Drawing Sheets

FIG. 2A

```
23                             53
atggttaataacaacagaccaagacgtcaacgagctcaacgcgttgtcgtcacaacaacc
 M  V  N  N  N  R  P  R  R  Q  R  A  Q  R  V  V  V  T  T  T 83                             113
caaacagcgcctgttccacagcaaaacgtgccacgtaatggtagacgccgacgtaatcgc
 Q  T  A  P  V  P  Q  Q  N  V  P  R  N  G  R  R  R  R  N  R 143                            173
acgaggcgtaatcgccgacgtgtgcgcggaatgaacatggcggcgctaaccagattaagt
 T  R  R  N  R  R  R  V  R  G  M  N  M  A  A  L  T  R  L  S 203                            233
caacctggtttggcgtttctcaaatgtgcatttgcaccacctgacttcaacaccgacccc
 Q  P  G  L  A  F  L  K  C  A  F  A  P  P  D  F  N  T  D  P 263                            293
ggtaagggaatacctgatagatttgaaggcaaagtggtcagccgaaaggatgtcctcaat
 G  K  G  I  P  D  R  F  E  G  K  V  V  S  R  K  D  V  L  N 323                            353
caatctatcagctttactgccggacaggacacttttatactcatcgcacctaccccggga
 Q  S  I  S  F  T  A  G  Q  D  T  F  I  L  I  A  P  T  P  G
                      ─────────
                         I1
383                            413
gtcgcctactggagtgctagcgttcctgctggtacttttcctactagtgcgactacgttt
 V  A  Y  W  S  A  S  V  P  A  G  T  F  P  T  S  A  T  T  F
                      ──────────────────────────────
                                   L3
443                            473
aaccccgttaattatccgggttttacatcgatgttcggaacaacttcaacatctaggtcc
 N  P  V  N  Y  P  G  F  T  S  M  F  G  T  T  S  T  S  R  S
                                  ──────────────────────────
                                              I2
503                            533
gatcaggtgtcctcattcaggtacgcttccatgaacgtgggtatttacccaacgtcgaac
 D  Q  V  S  S  F  R  Y  A  S  M  N  V  G  I  Y  P  T  S  N
 ───────────────
    I2 cont.
```

FIG. 2B

```
563                            593
ttgatgcagtttgccggaagcataactgtttggaaatgccctgtaaagctgagtactgtg
 L  M  Q  F  A  G  S  I  T  V  W  K  C  P  V  K  L  S  T  V
                                            ─────────────────
                                                   L1
623                            653
caattcccggttgcaacagatccagccaccagttcgctagttcatactcttgttggttta
 Q  F  P  V  A  T  D  P  A  T  S  S  L  V  H  T  L  V  G  L
─────────────────────────────────────────────
         L1 cont.
683                            713
gatggtgttctagcggtggggcctgacaacttctctgagtcattcatcaaaggagtgttt
 D  G  V  L  A  V  G  P  D  N  F  S  E  S  F  I  K  G  V  F
743                            773
tcacagtcggcttgtaacgagcctgactttgaattcaatgacatattggagggtatccag
 S  Q  S  A  C  N  E  P  D  F  E  F  N  D  I  L  E  G  I  Q
803                            833
acattgccacctgctaatgtgtcccttggttctacgggtcaacctttttaccatggactca
 T  L  P  P  A  N  V  S  L  G  S  T  G  Q  P  F  T  M  D  S
       ──────────────────────────────────────
                       L2
863                            893
ggagcagaagccaccagtggagtagtcggatggggcaatatggacacgattgtcatccgt
 G  A  E  A  T  S  G  V  V  G  W  N  M  D  T  I  V  I  R
923                            953
gtctcggcccctgagggcgcagttaactctgccatactcaaggcatggtcctgcattgag
 V  S  A  P  E  G  A  V  N  S  A  I  L  K  A  W  S  C  I  E
        ──────────────────────
                 I3
983                            1013
tatcgaccaaatccaaacgccatgttataccaattcggccatgattcgcctcctctcgat
 Y  R  P  N  P  N  A  M  L  Y  Q  F  G  H  D  S  P  P  L  D
1043                           1073
gaggtcgcgcttcaggaataccgtacggttgccagatctttgccggttgcagtgatagcg
 E  V  A  L  Q  E  Y  R  T  V  A  R  S  L  P  V  A  V  I  A
1103                           1133
gcccaaaatgcatcaatgtgggagagagtgaaatccatcattaaatcctccctggctgct
 A  Q  N  A  S  M  W  E  R  V  K  S  I  I  K  S  S  L  A  A
```

FIG. 2C

```
1163                           1193
gcaagcaacattcccggcccgatcggtgtcgccgcaagtggtattagtggactgtcagcc
 A  S  N  I  P  G  P  I  G  V  A  A  S  G  I  S  G  L  S  A 1223                           1253
ctttttgaaggatttggcttttagaagcatccggacgccaacctaaccgggcaagtatcc
 L  F  E  G  F  G  F  STOP 1283                           1313
gaacaatcggacatttggccacaataagcccaatttggttgaagattaaagtagtgagcc 1343                           1373
cccttagcgcgaaaccggaatttatattccaaaccagtttaagtcaacagactaagg
```

FIG. 3A

```
                                                              Alu I
                                                              Sac I   Mlu I
                                                              HgiA I
                                                    Hinc II  Ecl136 I         Afl III
                                                    BsaH I   Bsp1286 I
                         Drd I           Aat II Mae II  Ban II  BstU I  Mae III
Mse I
  |                        |               ||| |        ||      |        |      |
gtaaacaattccaagttccaaaatggttaataacaagaccaagagcgtcaacgcgttgtcgtcacaacaa
cattgttaaggttcaaggtttaccaattattgttctgttctcgcagttgcgcaacagcagtgttgtt
  ·         ·             ·               ·· ·         ·       ·        ·     ·
  27                      39             46 45       54       62      71   80
                                           45         54       61
                                             48       54       61
                                                      54
                                                      54
                                                      55
```

```
                                                                    Mae II
                                        Mae II                      Afl III
                                        BsaA I           Hga I
                     HinP I             PflM I           BsaH I
                     Hha I        Mae II Bsl I    Acc I         Mae II    Mnl I
          Tth111 II  Hae II       BspW I                                
          AlwN I     |||          |  |  |||       |  |   |  |   |        |
          |          ccaaacagcggcctgttccacagcaaaacgtgccacgtaatggtagagcgccgacgtaatcgcacgaggcgtaatcgccga  160
          gggtttgtcgcggacaaggtgtcgttttgcacggtgcattaccatctgcggctgcacggctgctccggcattagcggct  160
          83         87  89                 103   108  113   123   133          145          160
                      88                          113   126
                      89                                114
                                                        115
                                                        126
```

FIG. 3C

```
                                                         HinP I                    ScrF I
                                                         Hha I                     EcoR II
                                                         Hae II                    Dsa V
                                                         Fnu4H I                   BstN I
                                                         Aci I            Hinc II
Aci I                                                    |                |        |
BstU I           Nla III                                 |    Mse I       |   BstK I
HinP I           |                                       |    |           |   |
Hha I            |                                       |    |           |   |
|||              ||                                      |||  |           |   |
cgtgtgcgcggaatgaacatgggcgggctaaccagattaagtcaacctggttgcgtttctcaatgtgcatttgcacc 240
gcacacgcgccttacttgtaccgcccgattggtctaattcagttggaccaaacgcaaagagttacacgtaaacgtgg
         •        178       •       •    197   •    •
         166                182                201    206
         166                182                       206
         167                184                       206
         168                185                       206
                            185
```

FIG. 3D

```
         Msp I
         Hpa II
         ScrF I
         Ncl I
         Dsa V
         BstK I
         Bsl I
         Bcm I
         Bsl I
         BsaJ I                                                          Fok I   Mnl I
         |||        |                                                     |       |
acctgacttcaacaccgaccccggtaaggaataacctgatagatttgaaggcaaagtgttcagccgaaaggatgtcctca
tggactgaagttgtgtggctggggccattccccttatggactatctaaacttccgtttcaccagtcggctttcctacaggagt
         |||        |                                                      |       |
                  259                                                    310     316
                  259                                                                320
                  260
                  260
                  260
                  260
                  260
                  260
                  261
```

FIG. 3E

```
                                                                                      Bfa I
                                                        Msp I                         Nhe I       400
                                                        ScrF I                Bpm I    | |
                                                        Nci I                 Bsr I    | |
                                                        Dsa V                  | |
                                                        BstK I                 | |
                                                        Bcm I
                     Msp I                              BsaJ I  Hpa II
           Alu I     Hpa II                     Bsl I    | | |   | |
            | |       | |                        | |
atcaatctatcagctttactgccggacaggacactttatactcatcgcaccccggagtgcctactggagtgct
tagttagatagtcgaaatgacggcctgtcctgtgaaatatgagtagcgtggatggggcctcagcggatgacctcacga
  •                 •                            •         •                 •    •
  332               342                          371       377               390  398
                    342                                    377               391  399
                                                 376       377
                                                           377
                                                           378
                                                           378
                                                           381
                                                           381
```

FIG. 3G

```
                    Sau3A I
                    Mbo I
                    Dpn II
         Sau96 I    Dpn I                    Mnl I                           Mae II
         Ava II                              EcoN I       Rsa I      Nla III
    Bfa I                                    Bsl I        Csp6 I     BstX I   Mae III    Taq II   Bcq I
    |——————|—————————|——————————————————|———————|——————————|——|————————|——|———|———|——————|
aacaacttcaacatctaggtcgatcaggtgtcctcattcaggtacgcttccatgaacgtggtatttacccaacgtcga  560
ttgttgaagttgtagatccagctagtccacaggagtaagtccatgcgaaggtacttgcaccataaatgggttgcagct
    495       498                  503    513         523     531   537    554  557
              498                  503    513         523     532                    558
                                   503    513
```

FIG. 3H

```
                                                              Msp I
                                                              Hpa II
                                                              ScrF I
                                                              Nci I
                                        Rsa I                 Dsa V
                                        Csp6 I                BstK I                        BstY I
                                        Sca I                 Bcm I
                                  Dde I
              Msp I               Alu I
              Hpa II    Tth111 II
SfaN I
acttgatgcagtttgcccggaagcataactgtttggaaatgccctgtaaagctgagtactgtgcaattccggttgcaaca 640
tgaactacgtcaaacgggcctttcgtattgacaaaccttttacgggacatttcgactcatgacacgttaagggcaacgttgt
|—565        |—576                |—589      |—•609                            |—628      |—640
             |—576                                    611                       628
                                                      614                       628
                                                      615                       628
                                                      615                       629
```

FIG. 31

```
                                                          Ple I
                                                          Hinf I
                                  Sau96 I                 Dde I
                                  Nla IV
                          Act I   Hae III
                          Bfa I   EcoO109 I
Sau3A I                   |       |||
Mbo I                     |       |||                      |
Dpm II    Bsr I Bfa I     |       |||                      |
Dpm I     |     |         |       |||                      |
Alw I     |     |         |       |||                      |
|
gatccagccaccagttcgctagttcatactcttgttggtttagatggtgttgtttctagcggtgggcctgacaacttctctga  720
ctaggtcggtggtcaagcgatcaagtatgagaacaaccaaatctaccacaagatcgccacccggactgttgaagagact
641                                                                            717
641       651   659                              692      695  700              719
641                                                            700              719
641                                                            701
641                                                            702
```

```
                                                              Mnl I
                   Mae III                EcoR I
                   |                      Apo I               |
                   |                      |                   |
gtcattcattcaaaggagtgttttcacagtcggcttgtaacgagcctgactttgaattcaatgacatattggagggtatcc  800
cagtaagtagttcctcacaaaagtgtcagccgaacattgctcggactgaaacttaagttactgtataacctcccatagg
                   756                   773                 791
                                          773
```

FIG. 3K

```
                              Mnl I
                              Dde I        Mse I
                              Sau96 I      Hpa I
                              Nla IV  HinP I
                      Bsl I   Hae III Hha I
              BsaB I  Fok I   Bsu36 I Hinc II
      Drd I   BsmA I
Fok I
Mme I ggagtagtcggatgggcaatatggacacgattgtcatccgtctcgcgggcctgagggcgcagttaactctgccatact
cctcatcagcctaccccgttataccctgtgctaacagtaggcagagccgggactcccgcgtcaattgagacggtatga
     887        905       910    916  919    923   928    932      939  944
         890                                       928                  944
                                                   928             939    945
                                                        933
                                                         935
                                                                              960
```

FIG. 3L

```
                                                                    Tfi I
                                                                    Nla III
                                              Hae III       Mnl I    Taq I
                 Sau96 I                      Gdi II        Hinf I   Mnl I
                 Ava II            Taq I      Eae I
     Nla III
caaggcatggtcctgcattgagtatcgaccaatccaaacgccatgttataccaattcggccatgattcgcctcctctcg  1040
gttccgtaccaggacgtaactcatagctggttagttttgcggtacaatatggttaagccgtactaagcggaggagagc
     |—|                |—|                 |—|              |—|    |—|  |—|
     966                985                 Nla III           1025  1031  1038
     969                                    |—|               1025        1034
                                            1003              |—|
                                                              1018
                                                              1018
                                                              1019
                                                              1022
                                                              1025
```

FIG. 3M

```
         HinP I                                                                                    BspW I
         Hha I                            Sau3A I                                                  Sau96 I
         BstU I                           Mbo I                                                    Hae III
         Eco57 I              Rsa I       Dpn II                       BspW I                      Fnu4H I           SfaN I
Mnl I                         Csp6 I      Dpn I      Msp I                                         Aci I            Ppu10 I
                              BsiW I      BstY I     Hpa II                                                          Nsi I
                                          Bgl II     BsrF I
  |         |  |  |              |           |          |                |                            | |             |    1120
atgaggtcgcgcttcaggaatacggttacggttgccagatctttgccggttgcagtgatagcggcccaaatgcatcaatg
tactccagcgcgaagtccttatgccaatgccaacggtctagaaacggccaacgtcactatcgccgggtttttacgtagttac
  1043    1048 1052           1064        1076       1084              •                          1100 1110
         1049                 1065        1076       1085            1091                         1100 1110
         1049                 1065        1077       1085                                         1102       1112
                                          1077                                                   1102
                                          1077                                                   1103
                                          1077
                                          1077
```

FIG. 3N

```
                                                              Sau3A I
                                                              Sau96 I
                                                              Hae III
                      Fnu4H I                              Msp I    Mbo I
                ScrF I                                     Hpa II
                EcoR II                                    ScrF I    Dpn I
                Dsa V    Fnu4H I                           Nci I    Pvu I                Aci I
                BstN I                                     Dsa V    Mcr I                Fnu4H I
                BstK I                                     BstK I   Dpn I
          Mnl I  BsaJ I   Bbv I Tth111 II                  Bcm I    BsiE I
    Mse I  ─── ─── ─── ─── Bbv I ───                       ─── ─── ─── ─── ─── ─── ─── ───
    ─                                                                                                                1200
tgggagagagtgaaatgaaatcattaaatcctccctggctgctgcaagcaacattcccggccgatcggtgtcgccgcaag
acccctctctcacttaggtaattttaggtaattagtagtagttcgttgtgttgtaagggcggctagccacagcggcgttc
          1143   1149  1152 1157  1160  1164              1175  1182  1193
                                                           1175  1183  1194
                       1153       1160                     1175  1182
                       1153                                1175  1182
                       1153                                1175  1183
                       1153                                1176
                       1153           1157                 1176  1178
                                                                 1178
                                                                 1183
```

FIG. 3P

```
         Hae III                                      Mse I               BspW I   Dde I    Msp I
         Msc I                                        Mbo II     Bsp1286 I   BstU I   Apo I
         Hae I                                                   Ban II    HinP I   Hpa II
         Eae I                                                             Hha I    BsaW I ccgaacaatcggacatttggccacaataagcccaattggttgaagattaaagtagtgagcccccttagcgcgaaaccgg    1360
ggcttgttagcctgtaaaccggtgttattcgggttaaccaacttctaattcatcactcgggggaatcgcgcttttggcc
                                                                        ——  ——
        ——                                ——                        ——  1356 1357
      1298                              1323                      ——  1349 1357
      1298                              1328                    1338 1349 1350
      1298                                                      1338
      1299                                                      1340
                                                                1345

Mse I
                    Bsr I   Hinc II   Dde I
aatttatattccaaaccagtttaagtcaacagactaagt    1400
ttaaataaggttttggtcaaattcagttgtctgattcca
  ——      ——     ——    ——
1376     1381   1385  1394
```

FIG. 4A

| | | | | | | | |
|---|---|---|---|---|---|---|---|
| Aat II | 1 | Bsp1286I | 2 | Fse I | - | Pac I | - |
| Acc I | 1 | Bsp1407I | - | Fsp I | - | PaeR7 I | - |
| Acc65 I | - | BspD I | 1 | Gdi II | 1 | PflM I | 1 |
| Aci I | 5 | BspE I | 1 | Hae I | 1 | Ple I | 3 |
| Afl II | - | BspH I | - | Hae II | 2 | Pme I | - |
| Afl III | 2 | BspM I | 1 | Hae III | 6 | Pml I | - |
| Age I | - | BspW I | 4 | Hga I | 2 | Ppu10 I | 1 |
| Alu I | 3 | Bsr I | 4 | HgiA I | 1 | PpuM I | - |
| Alw I | 1 | BsrF I | 1 | Hha I | 6 | PshA I | - |
| AlwN I | 1 | BssH II | - | Hinc II | 5 | Psp1406I | - |
| Apa I | - | Bst1107I | - | Hind III | - | Pst I | - |
| ApaL I | - | BstB I | - | Hinf I | 4 | Pvu I | 1 |
| Apo I | 2 | BstE II | - | HinP I | 6 | Pvu II | - |
| Asc I | - | BstK I | 8 | Hpa I | 1 | Rsa I | 4 |
| Ase I | - | BstN I | 2 | Hpa II | 11 | Rsr II | - |
| Ava I | - | BstU I | 4 | Hph I | - | Sac I | 1 |
| Ava II | 2 | BstX I | 1 | Kas I | - | Sac II | - |
| Avr II | - | BstY I | 2 | Kpn I | - | Sal I | - |
| BamH I | - | Bsu36 I | 1 | Mae II | 8 | Sap I | - |
| Ban I | - | Cla I | 1 | Mae III | 2 | Sau3A I | 4 |
| Ban II | 2 | Csp6 I | 4 | Mbo I | 4 | Sau96 I | 6 |
| Bbe I | - | Dde I | 6 | Mbo II | 1 | Sca I | 1 |
| Bbs I | - | Dpn I | 4 | Mcr I | 1 | ScrF I | 8 |
| Bbv I | 2 | Dpn II | 4 | Mlu I | 1 | SfaN I | 3 |
| BceF I | - | Dra I | - | Mme I | 1 | Sfc I | - |
| Bcg I | 1 | Dra III | - | Mnl I | 9 | Sfi I | - |
| Bcl I | - | Drd I | 2 | Msc I | 1 | SgrA I | - |
| Bcn I | 6 | Dsa I | 1 | Mse I | 8 | Sma I | - |
| Bfa I | 5 | Dsa V | 8 | Msp I | 11 | SnaB I | - |
| Bgl I | - | Eae I | 2 | Mun I | - | Spe I | 1 |
| Bgl II | 1 | Eag I | - | Nae I | - | Sph I | - |
| Bpm I | 1 | Eam1105I | - | Nar I | - | Srf I | - |
| Bpu1102I | - | Ear I | - | Nci I | 6 | Sse8337I | - |
| Bsa I | - | Ecl136 I | 1 | Nco I | 1 | Ssp I | - |

FIG. 4B

| | | | | | | | |
|---|---|---|---|---|---|---|---|
| BsaA I | 1 | Eco47 III | – | Nde I | – | Stu I | – |
| BsaB I | 1 | Eco57 I | 1 | NgoM I | – | Sty I | 2 |
| BsaH I | 3 | EcoN I | 1 | Nhe I | 1 | Swa I | – |
| BsaJ I | 5 | EcoO109 I | 1 | Nla III | 6 | Taq I | 4 |
| BsaW I | 2 | EcoR I | 1 | Nla IV | 2 | Tfi I | 1 |
| Bsg I | – | EcoR II | 2 | Not I | – | Tth111 I | – |
| BsiE I | 1 | EcoR V | – | Nru I | – | Tth111 II | 3 |
| BsiW I | 1 | Ehe I | – | Nsi I | 1 | Xba I | – |
| Bsl I | 6 | Esp3 I | – | Nsp I | – | Xcm I | – |
| Bsm I | – | Fau I | – | Nsp7524 I | – | Xho I | – |
| BsmA I | 1 | Fnu4H I | 5 | NspB II | – | Xma I | – |
| Bsp120 I | – | Fok I | 4 | NspC I | – | Xmn I | 1 |

FIG. 5A

| | | | |
|---|---|---|---|
| Aat II | gacgt/c | 1 | 45 |
| Acc I | gt/mkac | 1 | 123 |
| Alw I | ggatc 4/5 | 1 | 641 |
| AlwN I | cagn3/ctg | 1 | 87 |
| Bcg I | cgan6tgc | 1 | 558 |
| Bgl II | a/gatct | 1 | 1076 |
| Bpm I | ctggag 16/14 | 1 | 391 |
| BsaA I | yac/gtr | 1 | 114 |
| BsaB I | gatnn/nnatc | 1 | 910 |
| BsiE I | cgry/cg | 1 | 1182 |
| BsiW I | c/gtacg | 1 | 1064 |
| BsmA I | gtctc 1/5 | 1 | 923 |
| BspD I | at/cgat | 1 | 469 |
| BspE I | t/ccgga | 1 | 1252 |
| BspM I | acctgc 4/8 | 1 | 811 |
| BsrF I | r/ccggy | 1 | 1084 |
| BstX I | ccan5/ntgg | 1 | 531 |
| Bsu36 I | cc/tnagg | 1 | 932 |
| Cla I | at/cgat | 1 | 469 |
| Dsa I | c/crygg | 1 | 852 |
| Ecl136 I | gag/ctc | 1 | 54 |
| Eco57 I | ctgaag 16/14 | 1 | 1052 |
| EcoN I | cctnn/n3agg | 1 | 513 |
| EcoO109 I | rg/gnccy | 1 | 700 |
| EcoR I | g/aattc | 1 | 773 |
| Gdi II | yggccg -5/-1 | 1 | 1018 |
| Hae I | wgg/ccw | 1 | 1298 |
| HgiA I | gwgcw/c | 1 | 54 |
| Hpa I | gtt/aac | 1 | 944 |
| Mbo II | gaaga 8/7 | 1 | 1323 |
| Mcr I | c/grycg | 1 | 1182 |
| Mlu I | a/cgcgt | 1 | 61 |
| Mme I | tccrac 20/18 | 1 | 887 |
| Msc I | tgg/cca | 1 | 1298 |

FIG. 5B

| | | | |
|---|---|---|---|
| Nco I | c/catgg | 1 | 852 |
| Nhe I | g/ctagc | 1 | 398 |
| Nsi I | atgca/t | 1 | 1110 |
| PflM I | ccan4/ntgg | 1 | 113 |
| Ppu10 I | a/tgcat | 1 | 1110 |
| Pvu I | cgat/cg | 1 | 1182 |
| Sac I | gagct/c | 1 | 54 |
| Sca I | agt/act | 1 | 614 |
| Spe I | a/ctagt | 1 | 425 |
| Tfi I | g/awtc | 1 | 1025 |
| Xmn I | gaann/nnttc | 1 | 480 |

| | | | | |
|---|---|---|---|---|
| Afl III | a/crygt | 2 | 61 | 160 |
| Apo I | r/aatty | 2 | 773 | 1360 |
| Ava II | g/gwcc | 2 | 498 | 969 |
| Ban II | grgcy/c | 2 | 54 | 1338 |
| Bbv I gcagc 8/12 | | 2 | 1157 | 1160 |
| BsaW I | w/ccggw | 2 | 1252 | 1356 |
| Bsp1286I | gdgch/c | 2 | 54 | 1338 |
| BstN I | cc/wgg | 2 | 206 | 1153 |
| BstY I | r/gatcy | 2 | 640 | 1076 |
| DrdI gacn4/nngtc | | 2 | 39 | 905 |
| Eae I | y/ggccr | 2 | 1018 | 1298 |
| EcoR II | /ccwgg | 2 | 206 | 1153 |
| Hae II | rgcgc/y | 2 | 88 | 184 |
| Hga I gacgc 5/10 | | 2 | 126 | 1256 |
| Mae III | /gtnac | 2 | 71 | 756 |
| Nla IV | ggn/ncc | 2 | 700 | 928 |
| Sty I | c/cwwgg | 2 | 826 | 852 |

| | | | | | |
|---|---|---|---|---|---|
| Alu I | ag/ct | 3 | 55 | 332 | 609 |
| BsaH I | gr/cgyc | 3 | 45 | 126 | 1256 |
| Ple I gagtc 4/5 | | 3 | 381 | 719 | 857 |
| SfaNI gcatc 5/9 | | 3 | 565 | 1112 | 1249 |
| Tth111II caarca 11/9 | | 3 | 83 | 589 | 1164 |
| BspWI gcn5/nngc | | 4 | 103 1091 | 1103 | 1340 |
| BsrI actgg 1/-1 | | 4 | 390 651 | 876 | 1376 |
| BstU I | cg/cg | 4 | 62 167 | 1048 | 1350 |

FIG. 5C

```
Csp6 I   g/tac       4    414 523 615 1065
Dpn I    ga/tc       4    503 641 1077 1183
Dpn II   /gatc       4    503 641 1077 1183
FokI   ggatg 9/13    4    310 890 916 1250
Hinf I   g/antc      4    381 719 857 1025
Mbo I    /gatc       4    503 641 1077 1183
Rsa I    gt/ac       4    414 523 615 1065
Sau3AI   /gatc       4    503 641 1077 1183
Taq I    t/cga       4    470 557 985 1038

Aci I   ccgc -3/-1   5    168 182 695 1100 1194
Bfa I    c/tag       5    399 426 495 659 692
BsaJ I   c/cnngg     5    259 376 826 852 1152
Fnu4H I  gc/ngc      5    182 1100 1157 1160 1193
Hinc II  gty/rac     5    48 201 840 944 1385

Bcn I    ccs/gg      6    260 377 458 628 1175 1269
Bsl I    ccn5/nngg   6    113 259 260 371 513 919
Dde I    c/tnag      6    611 717 859 933 1345 1394
Hae III  gg/cc       6    702 928 1019 1102 1178 1299
Hha I    gcg/c       6    89 166 185 939 1049 1349
HinP I   g/cgc       6    89 166 185 939 1049 1349
Nci I    cc/sgg      6    260 377 458 628 1175 1269
Nla III  catg/       6    178 532 853 966 1003 1022
Sau96 I  g/gncc      6    498 701 928 969 1102 1178

BstK I   c/cngg      8    206 260 377 458 628 1153 1175 1269
Dsa V    /ccngg      8    206 260 377 458 628 1153 1175 1269
Mae II   a/cgt       8    46 108 115 133 160 437 537 554
Mse I    t/taa       8    27 197 441 450 945 1143 1328 1381
ScrF I   cc/ngg      8    206 260 377 458 628 1153 1175 1269

MnlI    cctc 7/7     9    145 316 513 791 935 1031 1034 1043
                          1149
Hpa II   c/cgg      11    261 342 378 458 576 629 1085 1176
                          1253 1269 1357
Msp I    c/cgg      11    261 342 378 458 576 629 1085 1176
                          1253 1269 1357
```

FIG. 5D

| | | |
|---|---|---|
| Acc65I g/gtacc | DraIII cacn3/gtg | PmeI gttt/aaac |
| AflII c/ttaag | EagI c/ggccg | PmlI cac/gtg |
| AgeI a/ccggt | Eam1105I gacn3/nngtc | PpuMI rg/gwccy |
| ApaI gggcc/c | EarI ctcttc 1/4 | PshAI gacnn/nngtc |
| ApaLI g/tgcac | Eco47III agc/gct | Psp1406I aa/cgtt |
| AscI gg/cgcgcc | EcoRV gat/atc | PstI ctgca/g |
| AseI at/taat | EheI ggc/gcc | PvuII cag/ctg |
| AvaI c/ycgrg | Esp3I cgtctc 1/5 | RsrII cg/gwccg |
| AvrII c/ctagg | FauI cccgc 4/6 | SacII ccgc/gg |
| BamHI g/gatcc | FseI ggccgg/cc | SalI g/tcgac |
| BanI g/gyrcc | FspI tgc/gca | SapI gctcttc 1/4 |
| BbeI ggcgc/c | HindIII a/agctt | SfcI c/tryag |
| BbsI gaagac 2/6 | HphI ggtga 8/7 | SfiI ggccn4/nggcc |
| BceFI acggc12/13 | KasI g/gcgcc | SgrAI cr/ccggyg |
| BclI t/gatca | KpnI ggtac/c | SmaI ccc/ggg |
| BglI gccn4/nggc | MunI c/aattg | SnaBI tac/gta |
| Bpu1102I gc/tnagc | NaeI gcc/ggc | SphI gcatg/c |
| BsaI ggtctc1/5 | NarI gg/cgcc | SrfI gccc/gggc |
| BsgI gtgcag16/14 | NdeI ca/tatg | Sse8337I cctgca/gg |
| BsmI gaatgc 1/-1 | NgoMI g/ccggc | SspI aat/att |
| Bsp120I g/ggccc | NotI gc/ggccgc | StuI agg/cct |
| Bsp1407I t/gtaca | NruI tcg/cga | SwaI attt/aaat |
| BspHI t/catga | NspI rcatg/y | Tth111I gacn/nngtc |
| BssHII g/cgcgc | Nsp7524I r/catgy | XbaI t/ctaga |
| Bst1107I gta/tac | NspBII cmg/ckg | XcmI ccan5/n4tgg |
| BstBI tt/cgaa | NspCI rcatg/y | XhoI c/tcgag |
| BstEII g/gtnacc | PacI ttaat/taa | XmaI c/ccggg |
| DraI ttt/aaa | PaeR7I c/tcgag | |

FIG. 8

BACULOVIRUS DNA

POLYHEDRIN PROMOTER

FHV INSERT

↓ TRANSCRIPTION

5'  FHV-RNA 2  3'
AUG         UAG

↓ TRANSLATION

NH2 — COAT PRECURSOR PROTEIN — COOH

| Ag. for imm.<br>Ab titre | Ac NPV-V3<br>L3 | Ac NPV-V3<br>I3 | Ac NPV-V3<br>I3-L3 |
|---|---|---|---|
| FHV | 1:40000<br>1:20000<br>1:30000 | 1:20000<br>1:60000<br>1:10000 | 1:5000<br>1:15000<br>1:20000 |
| gp 120 | 1:500<br>1:1500<br>1:2000 | 1:2000<br>1:5000<br>1:1000 | 1:250<br>1:2000<br>1:500 |

FIG. 16

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
        (A) LENGTH: 1400 base pairs
        (B) TYPE: nucleic acid
        (C) STRANDEDNESS: single
        (D) TOPOLOGY: linear (xi) SEQUENCE DESCRIPTION: SEQ ID NO:1:

```
GTAAACAATT CCAAGTTCCA AAATGGTTAA TAACAACAGA CCAAGACGTC AACGAGCTCA      60

ACGCGTTGTC GTCACAACAA CCCAAACAGC GCCTGTTCCA CAGCAAAACG TGCCACGTAA     120

TGGTAGACGC CGACGTAATC GCACGAGGCG TAATCGCCGA CGTGTGCGCG GAATGAACAT     180

GGCGGCGCTA ACCAGATTAA GTCAACCTGG TTTGGCGTTT CTCAAATGTG CATTTGCACC     240

ACCTGACTTC AACACCGACC CCGGTAAGGG AATACCTGAT AGATTTGAAG GCAAAGTGGT     300

CAGCCGAAAG GATGTCCTCA ATCAATCTAT CAGCTTTACT GCCGGACAGG ACACTTTTAT     360

ACTCATCGCA CCTACCCCCG GAGTCGCCTA CTGGAGTGCT AGCGTTCCTG CTGGTACTTT     420

TCCTACTAGT GCGACTACGT TTAACCCCGT TAATTATCCG GGTTTTACAT CGATGTTCGG     480

AACAACTTCA ACATCTAGGT CCGATCAGGT GTCCTCATTC AGGTACGCTT CCATGAACGT     540

GGGTATTTAC CCAACGTCGA ACTTGATGCA GTTTGCCGGA AGCATAACTG TTTGGAAATG     600

CCCTGTAAAG CTGAGTACTG TGCAATTCCC GGTTGCAACA GATCCAGCCA CCAGTTCGCT     660

AGTTCATACT CTTGTTGGTT TAGATGGTGT TCTAGCGGTG GGGCCTGACA ACTTCTCTGA     720

GTCATTCATC AAAGGAGTGT TTTCACAGTC GGCTTGTAAC GAGCCTGACT TTGAATTCAA     780

TGACATATTG GAGGGTATCC AGACATTGCC ACCTGCTAAT GTGTCCCTTG GTTCTACGGG     840

TCAACCTTTT ACCATGGACT CAGGAGCAGA AGCCACCAGT GGAGTAGTCG GATGGGGCAA     900

TATGGACACG ATTGTCATCC GTGTCTCGGC CCCTGAGGGC GCAGTTAACT CTGCCATACT     960

CAAGGCATGG TCCTGCATTG AGTATCGACC AAATCCAAAC GCCATGTTAT ACCAATTCGG    1020

CCATGATTCG CCTCCTCTCG ATGAGGTCGC GCTTCAGGAA TACCGTACGG TTGCCAGATC    1080

TTTGCCGGTT GCAGTGATAG CGGCCCAAAA TGCATCAATG TGGGAGAGAG TGAAATCCAT    1140

CATTAAATCC TCCCTGGCTG CTGCAAGCAA CATTCCCGGC CCGATCGGTG TCGCCGCAAG    1200

TGGTATTAGT GGACTGTCAG CCCTTTTTGA AGGATTTGGC TTTTAGAAGC ATCCGGACGC    1260

CAACCTAACC GGGCAAGTAT CCGAACAATC GGACATTTGG CCACAATAAG CCCAATTTGG    1320

TTGAAGATTA AAGTAGTGAG CCCCCTTAGC GCGAAACCGG AATTTATATT CCAAACCAGT    1380

TTAAGTCAAC AGACTAAGGT                                               1400
```

(2) INFORMATION FOR SEQ ID NO:2:

(i) SEQUENCE CHARACTERISTICS:
        (A) LENGTH: 1378 base pairs
        (B) TYPE: nucleic acid
        (C) STRANDEDNESS: single
        (D) TOPOLOGY: linear (ix) FEATURE:
    (A) NAME/KEY: CDS
    (B) LOCATION: 1..1221

(xi) SEQUENCE DESCRIPTION: SEQ ID NO:2:

```
ATG GTT AAT AAC AAC AGA CCA AGA CGT CAA CGA GCT CAA CGC GTT GTC      48
Met Val Asn Asn Asn Arg Pro Arg Arg Gln Arg Ala Gln Arg Val Val
  1               5                  10                  15

GTC ACA ACA ACC CAA ACA GCG CCT GTT CCA CAG CAA AAC GTG CCA CGT      96
Val Thr Thr Thr Gln Thr Ala Pro Val Pro Gln Gln Asn Val Pro Arg
                 20                  25                  30

AAT GGT AGA CGC CGA CGT AAT CGC ACG AGG CGT AAT CGC CGA CGT GTG     144
Asn Gly Arg Arg Arg Arg Asn Arg Thr Arg Arg Asn Arg Arg Arg Val
             35                  40                  45

CGC GGA ATG AAC ATG GCG GCG CTA ACC AGA TTA AGT CAA CCT GGT TTG     192
Arg Gly Met Asn Met Ala Ala Leu Thr Arg Leu Ser Gln Pro Gly Leu
         50                  55                  60

GCG TTT CTC AAA TGT GCA TTT GCA CCA CCT GAC TTC AAC ACC GAC CCC     240
Ala Phe Leu Lys Cys Ala Phe Ala Pro Pro Asp Phe Asn Thr Asp Pro
 65                  70                  75                  80

GGT AAG GGA ATA CCT GAT AGA TTT GAA GGC AAA GTG GTC AGC CGA AAG     288
Gly Lys Gly Ile Pro Asp Arg Phe Glu Gly Lys Val Val Ser Arg Lys
                 85                  90                  95

GAT GTC CTC AAT CAA TCT ATC AGC TTT ACT GCC GGA CAG GAC ACT TTT     336
Asp Val Leu Asn Gln Ser Ile Ser Phe Thr Ala Gly Gln Asp Thr Phe
            100                 105                 110

ATA CTC ATC GCA CCT ACC CCC GGA GTC GCC TAC TGG AGT GCT AGC GTT     384
Ile Leu Ile Ala Pro Thr Pro Gly Val Ala Tyr Trp Ser Ala Ser Val
        115                 120                 125

CCT GCT GGT ACT TTT CCT ACT AGT GCG ACT ACG TTT AAC CCC GTT AAT     432
Pro Ala Gly Thr Phe Pro Thr Ser Ala Thr Thr Phe Asn Pro Val Asn
130                 135                 140

TAT CCG GGT TTT ACA TCG ATG TTC GGA ACA ACT TCA ACA TCT AGG TCC     480
Tyr Pro Gly Phe Thr Ser Met Phe Gly Thr Thr Ser Thr Ser Arg Ser
145                 150                 155                 160

GAT CAG GTG TCC TCA TTC AGG TAC GCT TCC ATG AAC GTG GGT ATT TAC     528
Asp Gln Val Ser Ser Phe Arg Tyr Ala Ser Met Asn Val Gly Ile Tyr
                165                 170                 175

CCA ACG TCG AAC TTG ATG CAG TTT GCC GGA AGC ATA ACT GTT TGG AAA     576
Pro Thr Ser Asn Leu Met Gln Phe Ala Gly Ser Ile Thr Val Trp Lys
            180                 185                 190

TGC CCT GTA AAG CTG AGT ACT GTG CAA TTC CCG GTT GCA ACA GAT CCA     624
Cys Pro Val Lys Leu Ser Thr Val Gln Phe Pro Val Ala Thr Asp Pro
        195                 200                 205

GCC ACC AGT TCG CTA GTT CAT ACT CTT GTT GGT TTA GAT GGT GTT CTA     672
Ala Thr Ser Ser Leu Val His Thr Leu Val Gly Leu Asp Gly Val Leu
    210                 215                 220

GCG GTG GGG CCT GAC AAC TTC TCT GAG TCA TTC ATC AAA GGA GTG TTT     720
Ala Val Gly Pro Asp Asn Phe Ser Glu Ser Phe Ile Lys Gly Val Phe
225                 230                 235                 240

TCA CAG TCG GCT TGT AAC GAG CCT GAC TTT GAA TTC AAT GAC ATA TTG     768
Ser Gln Ser Ala Cys Asn Glu Pro Asp Phe Glu Phe Asn Asp Ile Leu
                245                 250                 255

GAG GGT ATC CAG ACA TTG CCA CCT GCT AAT GTG TCC CTT GGT TCT ACG     816
Glu Gly Ile Gln Thr Leu Pro Pro Ala Asn Val Ser Leu Gly Ser Thr
            260                 265                 270

GGT CAA CCT TTT ACC ATG GAC TCA GGA GCA GAA GCC ACC AGT GGA GTA     864
Gly Gln Pro Phe Thr Met Asp Ser Gly Ala Glu Ala Thr Ser Gly Val
        275                 280                 285

GTC GGA TGG GGC AAT ATG GAC ACG ATT GTC ATC CGT GTC TCG GCC CCT     912
```

-continued

```
                Val Gly Trp Gly Asn Met Asp Thr Ile Val Ile Arg Val Ser Ala Pro
                    290                 295                 300

GAG GGC GCA GTT AAC TCT GCC ATA CTC AAG GCA TGG TCC TGC ATT GAG              960
Glu Gly Ala Val Asn Ser Ala Ile Leu Lys Ala Trp Ser Cys Ile Glu
305                 310                 315                 320

TAT CGA CCA AAT CCA AAC GCC ATG TTA TAC CAA TTC GGC CAT GAT TCG             1008
Tyr Arg Pro Asn Pro Asn Ala Met Leu Tyr Gln Phe Gly His Asp Ser
                325                 330                 335

CCT CCT CTC GAT GAG GTC GCG CTT CAG GAA TAC CGT ACG GTT GCC AGA             1056
Pro Pro Leu Asp Glu Val Ala Leu Gln Glu Tyr Arg Thr Val Ala Arg
            340                 345                 350

TCT TTG CCG GTT GCA GTG ATA GCG GCC CAA AAT GCA TCA ATG TGG GAG             1104
Ser Leu Pro Val Ala Val Ile Ala Ala Gln Asn Ala Ser Met Trp Glu
        355                 360                 365

AGA GTG AAA TCC ATC ATT AAA TCC TCC CTG GCT GCT GCA AGC AAC ATT             1152
Arg Val Lys Ser Ile Ile Lys Ser Ser Leu Ala Ala Ala Ser Asn Ile
370                 375                 380

CCC GGC CCG ATC GGT GTC GCC GCA AGT GGT ATT AGT GGA CTG TCA GCC             1200
Pro Gly Pro Ile Gly Val Ala Ala Ser Gly Ile Ser Gly Leu Ser Ala
385                 390                 395                 400

CTT TTT GAA GGA TTT GGC TTT TAGAAGCATC CGGACGCCAA CCTAACCGGG                 1251
Leu Phe Glu Gly Phe Gly Phe
                405

CAAGTATCCG AACAATCGGA CATTTGGCCA CAATAAGCCC AATTTGGTTG AAGATTAAAG           1311

TAGTGAGCCC CCTTAGCGCG AAACCGGAAT TTATATTCCA AACCAGTTTA AGTCAACAGA           1371

CTAAGGT                                                                    1378

(2) INFORMATION FOR SEQ ID NO:3:

(i) SEQUENCE CHARACTERISTICS:
        (A) LENGTH: 407 amino acids
        (B) TYPE: amino acid
        (D) TOPOLOGY: linear (ii) MOLECULE TYPE: protein (xi) SEQUENCE DESCRIPTION: SEQ ID NO:3:

Met Val Asn Asn Asn Arg Pro Arg Arg Gln Arg Ala Gln Arg Val Val
1               5                   10                  15

Val Thr Thr Thr Gln Thr Ala Pro Val Pro Gln Gln Asn Val Pro Arg
                20                  25                  30

Asn Gly Arg Arg Arg Asn Arg Thr Arg Arg Asn Arg Arg Val
            35                  40                  45

Arg Gly Met Asn Met Ala Ala Leu Thr Arg Leu Ser Gln Pro Gly Leu
        50                  55                  60

Ala Phe Leu Lys Cys Ala Phe Ala Pro Pro Asp Phe Asn Thr Asp Pro
65                  70                  75                  80

Gly Lys Gly Ile Pro Asp Arg Phe Glu Gly Lys Val Val Ser Arg Lys
                85                  90                  95

Asp Val Leu Asn Gln Ser Ile Ser Phe Thr Ala Gly Gln Asp Thr Phe
                100                 105                 110

Ile Leu Ile Ala Pro Thr Pro Gly Val Ala Tyr Trp Ser Ala Ser Val
            115                 120                 125

Pro Ala Gly Thr Phe Pro Thr Ser Ala Thr Thr Phe Asn Pro Val Asn
        130                 135                 140

Tyr Pro Gly Phe Thr Ser Met Phe Gly Thr Thr Ser Thr Ser Arg Ser
145                 150                 155                 160

Asp Gln Val Ser Ser Phe Arg Tyr Ala Ser Met Asn Val Gly Ile Tyr
```

```
                        165                 170                 175
    Pro Thr Ser Asn Leu Met Gln Phe Ala Gly Ser Ile Thr Val Trp Lys
                    180                 185                 190

Cys Pro Val Lys Leu Ser Thr Val Gln Phe Pro Val Ala Thr Asp Pro
                195                 200                 205

Ala Thr Ser Ser Leu Val His Thr Leu Val Gly Leu Asp Gly Val Leu
            210                 215                 220

Ala Val Gly Pro Asp Asn Phe Ser Glu Ser Phe Ile Lys Gly Val Phe
    225                 230                 235                 240

Ser Gln Ser Ala Cys Asn Glu Pro Asp Phe Glu Phe Asn Asp Ile Leu
                    245                 250                 255

Glu Gly Ile Gln Thr Leu Pro Pro Ala Asn Val Ser Leu Gly Ser Thr
                260                 265                 270

Gly Gln Pro Phe Thr Met Asp Ser Gly Ala Glu Ala Thr Ser Gly Val
            275                 280                 285

Val Gly Trp Gly Asn Met Asp Thr Ile Val Ile Arg Val Ser Ala Pro
    290                 295                 300

Glu Gly Ala Val Asn Ser Ala Ile Leu Lys Ala Trp Ser Cys Ile Glu
    305                 310                 315                 320

Tyr Arg Pro Asn Pro Asn Ala Met Leu Tyr Gln Phe Gly His Asp Ser
                    325                 330                 335

Pro Pro Leu Asp Glu Val Ala Leu Gln Glu Tyr Arg Thr Val Ala Arg
                340                 345                 350

Ser Leu Pro Val Ala Val Ile Ala Ala Gln Asn Ala Ser Met Trp Glu
                355                 360                 365

Arg Val Lys Ser Ile Ile Lys Ser Ser Leu Ala Ala Ser Asn Ile
    370                 375                 380

Pro Gly Pro Ile Gly Val Ala Ala Ser Gly Ile Ser Gly Leu Ser Ala
    385                 390                 395                 400

Leu Phe Glu Gly Phe Gly Phe
                    405

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:4:

Met Gly Thr Asn Leu Ser Val Pro Asn Pro Pro Ala Phe Gly Ala Asn
1               5                   10                  15

Ser Thr Asn Pro Asp Trp Asp Phe Asn Pro Gly Gly Met Gln Trp Asn
            20                  25                  30

Ser Thr Ala Leu
        35

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:5:

Met Gln Trp Asn Ser Thr Ala Leu Asp Pro Arg Val Arg Gly Leu
1               5                   10                  15
```

(2) INFORMATION FOR SEQ ID NO:6:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:6:

```
Cys Thr Thr Pro Ala Gln Gly Asn Ser Met Phe Pro Ser Cys Cys Cys
1               5                   10                  15
Thr Lys Pro Thr Asp Gly Asn Cys
            20
```

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:7:

```
Thr Asn Pro Lys Pro Gln Arg Lys Thr Lys Arg Asn Thr Asn Arg Arg
1               5                   10                  15
Pro Gln Asp Pro Arg Arg
            20
```

(2) INFORMATION FOR SEQ ID NO:8:

(i) SEQUENCE CHARACTERISTICS:
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO:8:

```
Val Lys Phe Pro Gly Gly Gly Gln Ile Val Gly Gly Val Tyr Leu Leu
1               5                   10                  15
Pro Arg Arg
```

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:9:

```
Ile Gln Arg Gly Pro Gly Arg Ala Phe
1               5
```

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:10:

```
Ile Gly Pro Gly Arg Ala Phe
1               5
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:11:

Phe Gly Pro Gly Gln Ala Leu
1               5

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:12:

Ile Gly Pro Gly Arg Thr Leu
1               5

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:13:

Lys Gly Pro Gly Arg Val Ile
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:14:

Ile Gly Leu Gly Gln Ala Leu
1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:15:

Gly Lys Ala Met Tyr Ala Pro Pro Ile
1               5

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:16:

-continued

```
Asn Met Trp Gln Glu Lys Val Gly Lys Ala
1               5                   10

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:17:

Glu Leu Asp Lys Trp Ala Ser
1               5

(2) INFORMATION FOR SEQ ID NO:18:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:18:

Ile Glu Glu Glu Gly Gly Glu Arg Asp Arg Asp Arg
1               5                   10

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:19:

Ile Gly Pro Gly Arg Ala Phe Glu
1               5

(2) INFORMATION FOR SEQ ID NO:20:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:20:

Gly Pro Gly Arg Ala Phe
1               5
```

MOLECULAR PRESENTING SYSTEM

CROSS REFERENCE TO RELATED APPLICATIONS

This application claims benefit to PCT/EP95/03114 filed on Aug. 4, 1995, which claims priority to Austrian Application No. A 1545/94 filed on Aug. 8, 1994, both of which are incorporated in their entirety.

TECHNICAL FIELD

The invention concerns a molecular presentation system in which viral proteins are being used as carriers for heterologous amino acid sequences.

BACKGROUND OF THE INVENTION

The possibility to identify and synthesize amino acid sequences from viral proteins, which are able to generate a protective immune response in animals, has stimulated the development of synthetic vaccines. Although it has already been shown that synthetic peptides in some cases can induce a good immune response, it has turned out that in general they were weak immunogens unless coupled to strongly immunogenic carrier molecules. They were frequently unable to induce protective immunity in vaccinated animals. Attempts to increase the immunogenicity of these antigens for use as vaccine have lead to the development of a series of antigen presentation systems. Many of these are designed to present the antigen as a polyvalent, particulate structure. The development of particulate vector systems for immunogenic epitopes provides a powerful approach for the presentation of antigens. Various systems were used to present foreign epitopes: the core antigen of Hepatitis B virus (HBV) (HBcAg) [1] and the surface antigen of Hepatitis B virus (HBsAg) [2], the capside protein from Polio virus [3], the yeast Ty protein [4], the particles obtained after insertion of HIV 1-gag in Baculovirus [5], rotavirus VP-6 protein [6], core particles of the Bluetongue virus (BTV) [7], and filamentous as well as icosahedral bacteriophages [8,9].

It has been demonstrated that the immunogenicity of a peptide depends on its sequence as well as on the way it is presented to the immune system. By using a human rhino virus capsid sequence as a heterologous peptide and the particles of HBcAg as a carrier, it was shown that the internal location of the foreign sequence increases the immunogenicity of the epitope by 10 to 50 fold when compared to the amino terminus location [10]. Also the antigenicity (measured as reactivity to a monoclonal antibody (mAb)) was greatly enhanced by placing the foreign peptide in that position in the carrier. Furthermore, both constructs presented the epitopes considerably more efficiently to the mAbs than the free peptides. This was also the case when specific HIV-1 epitopes (the V3 loop) were introduced into different domains of the HBcAg [11]. Since the properties of a given epitope can be influenced by its conformation it was of great interest to have a carrier system with multiple entry sites conferring many possible conformations. This would increase the possibility of finding a conformation closer to the native one for a given sequence. In spite of the fact that, as mentioned above, various particulate systems have been developed for the presentation of epitopes, they were all based on the foreign epitope being inserted mainly in one position. This was partly due to lack of knowledge about the 3-D structure of the carrier particle.

SUMMARY OF THE INVENTION

With reference to the above, a new presentation system has been developed, characterized by the fact that the carrier protein is derived from small insect viruses, Flock House virus (FHV), with a known 3-D structure and amino acid sequence. Heterologous amino acid sequences, for example epitopes, are inserted into the outwards directed loops of the viral capsid protein. This carrier presents multiple possibilities for a conformationally suitable location of epitopes. Above all, the carrier system is characterized by the fact that the recombinant protein, or the virus like particles, are obtained from procaryotic or eucaryotic cells through the expression of the protein encoded by the appropriately modified RNA-2 gene of the FHV capsid protein.

BRIEF DESCRIPTION OF THE DRAWINGS

FIGS. 2A–2C depict the DNA and amino acid sequences of FHV RNA-2 with the individual loops (L1, L2, L3, I1, I2 and I3) shown in bold type.

FIGS. 4A–4B depict the number of restriction endonuclease usage sites in the FHV RNA-2.

FIGS. 5A–5D depict all of the restriction endonuclease sites in the FHV RNA-2.

FIG. 8 depicts a representation of FHV capsomer virus-like particles produced in Baculovirus.

FIG. 9A shows SF-21 infected cell lysates analyzed in 10% SDS-PAGE and stained with Coomassie blue. FIG. 9B shows SF-21 infected cell lysates analyzed by Western blot with (1) an antiserum against FHV; (2) a human HIV-1 monoclonal antibody; (3 and 4) a HIV-1 positive sera and (5) a HIV-1 negative serum.

FIG. 10A depicts AcNPV-FHV which expresses the unmodified FHV capsid protein. FIG. 10B depicts AcNPV-FHV-V3/L1 expressing the same protein carrying the HIV-1 epitope in position L1. FIG. 10C depicts AcNPV-FHV-V3/L2 expressing the same protein carrying the HIV-1 epitope in position L2.

FIG. 11 depicts serum anti-V3 antibody titers measured against recombinant gp120.

FIGS. 15A–15D show the results of 4 out of 50 patients which were analyzed. The RIB II values are shown in the upper panel of each of the figures. The VLP-based ELISA test values are represented in the diagrams as circles. The ALT values are represented in the diagrams as a vertical line.

FIG. 16 depicts the detection of HCV core-antibodies in human sera by dot-blots using recombinant (VLP-HCV) antigen or free peptides. Lanes 1–6 show patients' sera and lane NC shows the negative control serum.

DETAILED DESCRIPTION OF THE INVENTION

Characteristics of the Carrier Particle

Flock House Virus (FHV)

FHV is a non-enveloped icosahedrical insect virus with a bipartite RNA genome and belonging to the Nodaviridae family. These viruses are among the smallest and simplest known. The FHV genome consists of two single stranded mRNA molecules (RNA-1 with 3.1 kb and RNA-2 with 1.4 kb), both encapsidated in the same particle. RNA-1 carries the information for the viral RNA-polymerase and RNA-2 codes for the coat precursor, alpha protein. Upon synthesis the coat precursor alpha is rapidly assembled with both RNAs, whereby immature, virion-like particles (provirions) are formed. These are slowly processed to mature particles by autocatalytic cleavages [12].

Figure 1:
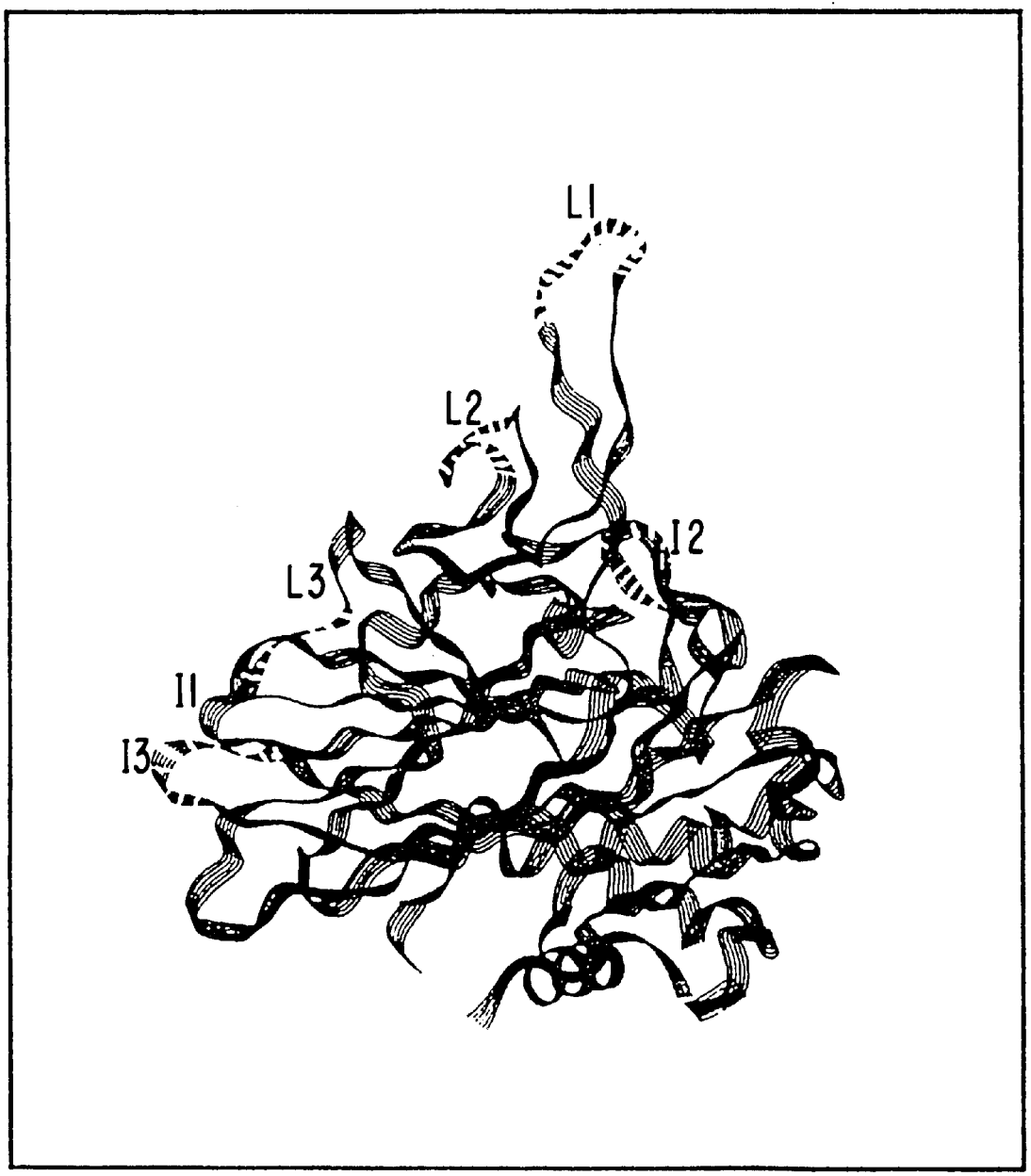
FIG. 1 illustrates a crystallographic representation of the outward directed loops of the FHV capsid protein precursor with 3 Angstrom resolution showing the positions of insertions of the foreign genes (L1, L2, L3, I1, I2 and I3).
Figure 3F:
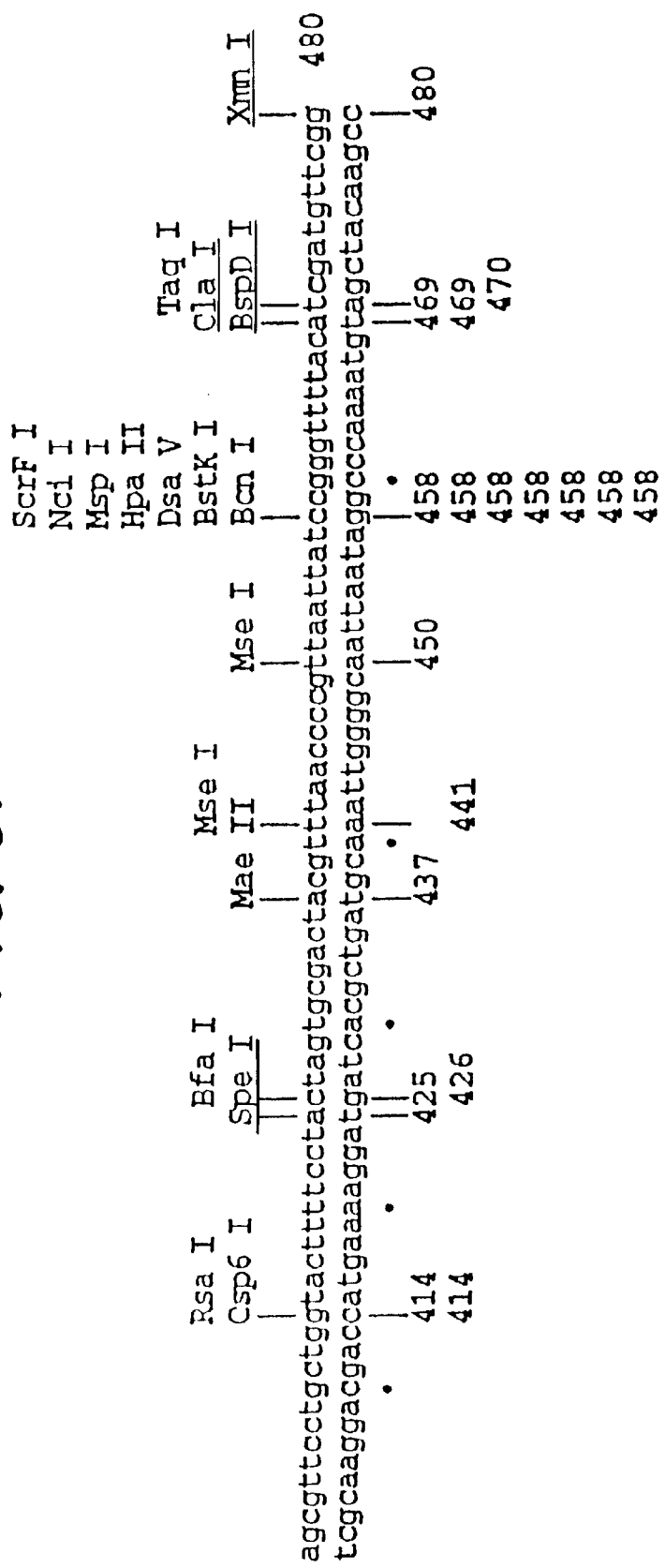
FIGS. 3A–3F depict the full restriction map of the DNA sequence of FHV RNA-2.
Figure 3J:
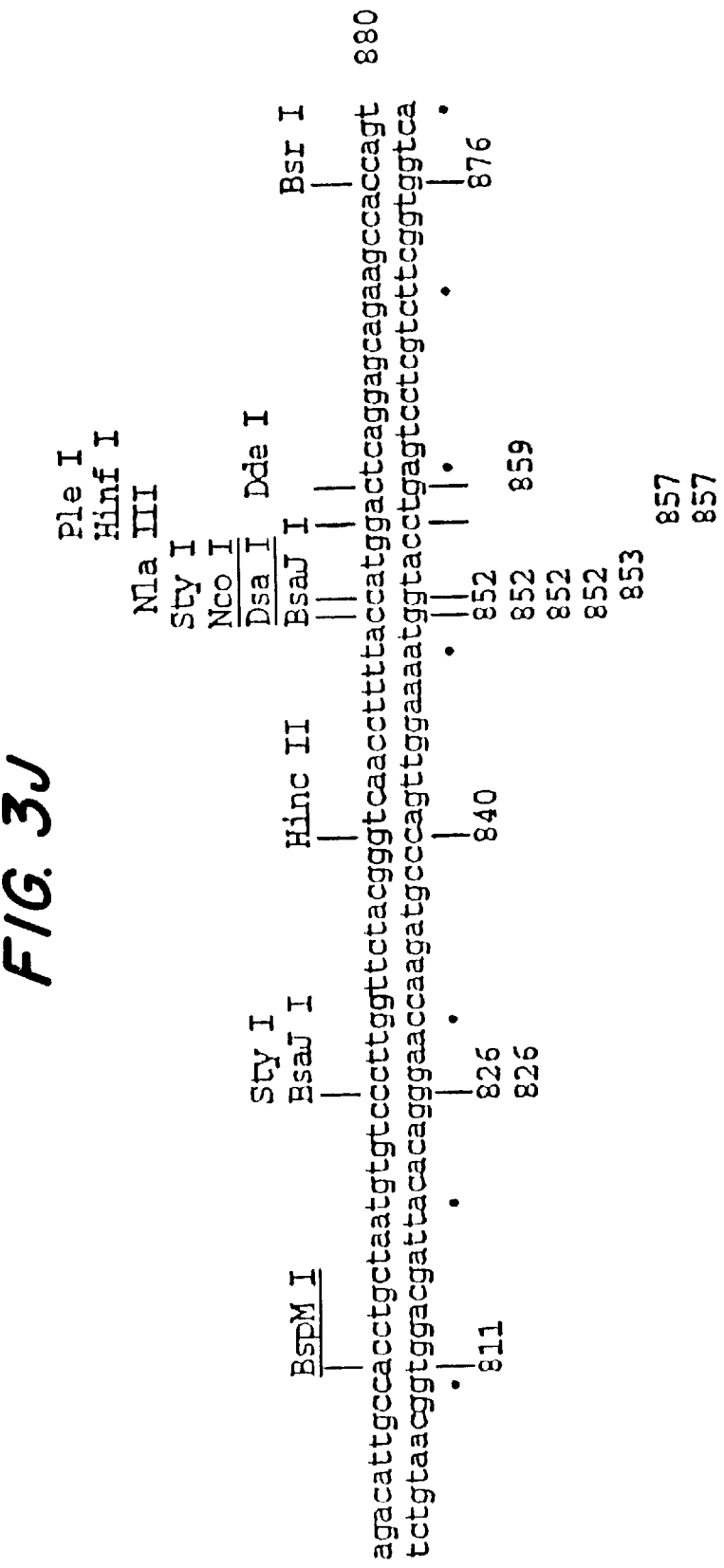
Figure 30:
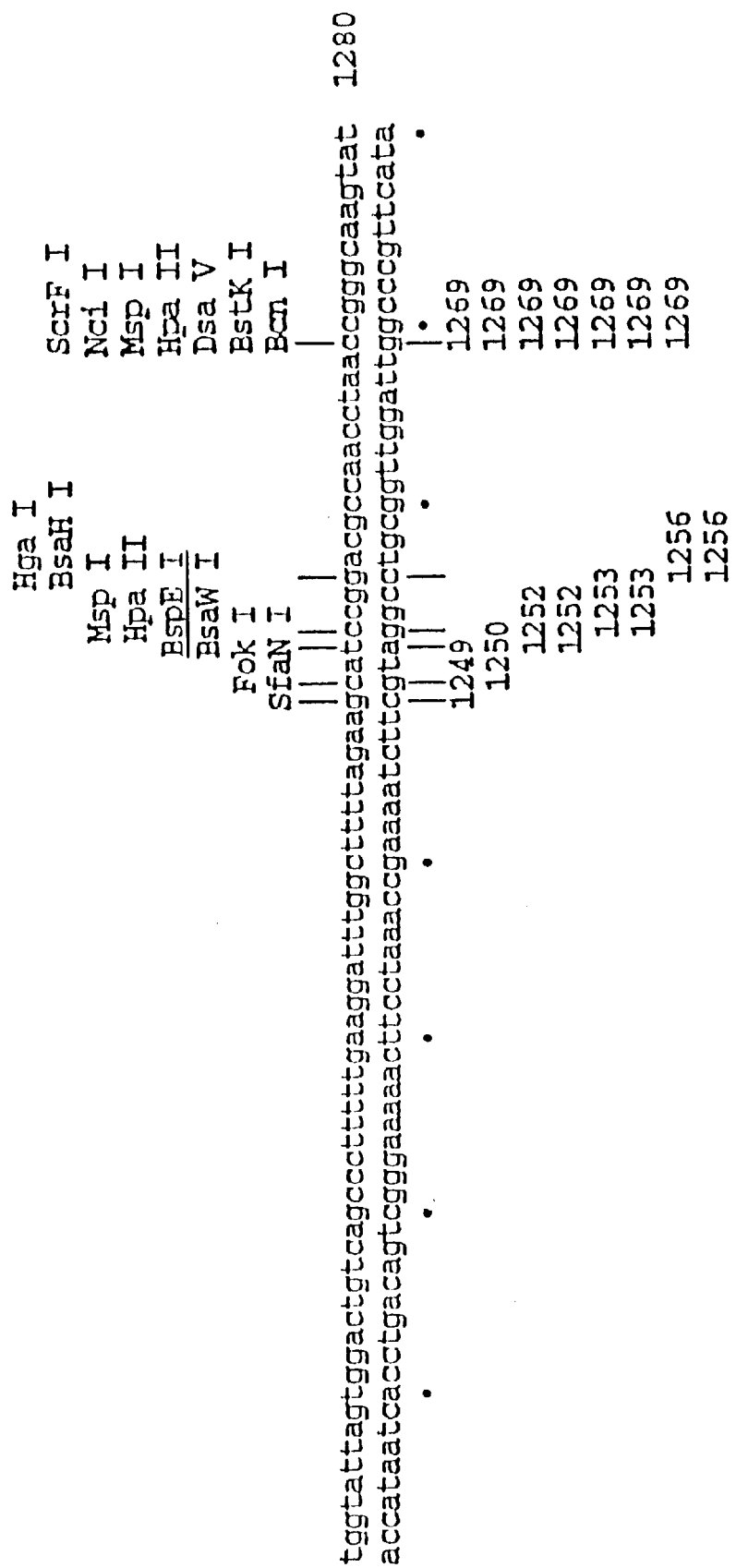

X-ray diffraction studies have shown the structure of the viral particles at 3.0 Angstrom resolution [13] (see FIG. 1). The virion has 60 icosahedrical, asymmetric units each consisting of three quasiequivalent protomers forming a protein shell around the inner RNA genome [14]. The protomers consist of 1) a basic, crystallographically disordered aminoterminus, 2) a Beta-barrel structure, 3) an outer protrusion composed predominantly of Beta sheets and formed by three large insertions between the strands of the Beta-barrel, and 4) a carboxyterminal domain composed of two distorted helices lying inside the shell. The external zone of the virion, which is the least conserved, has many sequence differences which essentially contain all the deletions and insertions of the different strains [12]. The variations in the loops, directed outwards from the segments of the Beta-barrel structure, define serologically distinct viral strains.

These loops were selected as the regions to be manipulated for the insertion of the foreign epitopes. The positions for these insertions (L1, L2, L3, I1, I2, I3,) are given by the following amino acid regions of the RNA 2 gene:

Loop L1 amino acids 195–219
Loop L2 amino acids 263–277
Loop L3 amino acids 129–138
Loop I1 amino acids 107–110
Loop I2 amino acids 152–165
Loop I3 amino acids 304–310

FIGS. 2A–2C show the DNA sequence of FHV RNA-2 and the corresponding amino acid sequence (SEQ ID NOS:2 and 3), the individual loop regions are bolded.

FIGS. 3A–3E show the full restriction map of the DNA sequence of FHV RNA-2 (SEQ ID NO:1).

FIGS. 4A–4B represent the number of cutting sites of the endonucleases.

FIGS. 5A–5D show all sites in which the endonucleases cut FHV RNA-2.

Figure 6:
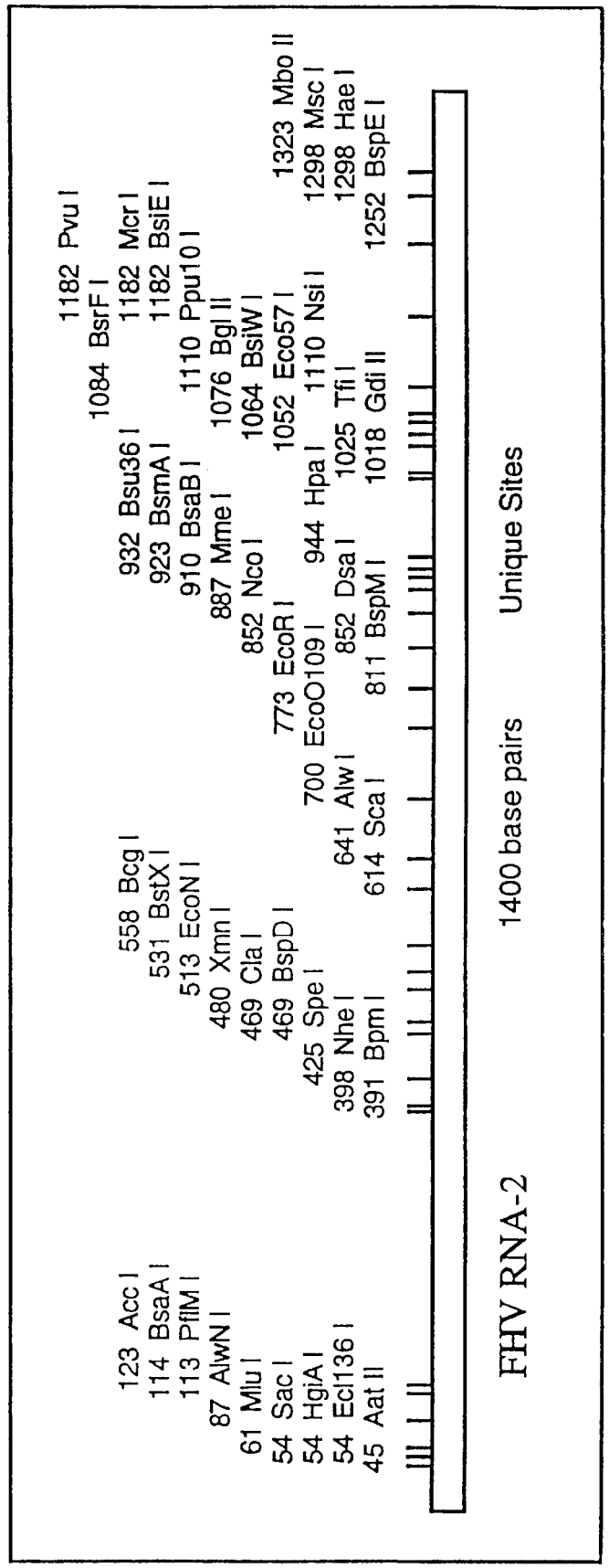
FIG. 6 is a graphic representation of the unique endonuclease sites in the FHV RNA-2.

FIG. 6 is a graphic representation of the unique cutting sites of the endonucleases.

FHV grows vigorously in cultured cells and produces yields of 20% of the total cell protein [14]. In addition, FHV grows well in several Lepitopteran larvae. The viruses of this family show a considerable resistance to inactivation by heat, detergents and other denaturants [14]. It was shown recently [15] that the expression of the capside protein FHV RNA-2 in insect cells via a recombinant baculovirus produces virion like particles (VLP) similar to authentic virions. It was shown by the present inventors that this can also be achieved by the expression of a modified gene carrying insertions for the expression of foreign amino acids within the capsomer structure. The VLPs generated by this procedure in insect cells are mature particles since the precursor protein, which is present in provirions, is cleaved. This system allows the production of 1–2 mg of purified synthetic virions (VLPs) in 50 ml of cultured cells [16].

Another method for the production of particles carrying foreign epitopes is by recovery of infectious virions after cotransfection of the genomic RNA-2 (obtained by in vitro transcription of modified cDNAs) with purified RNA-1 [17]. This is only valid for genomes which carry alterations that do not change the replicative cycle or the assembly of the virus. The RNA-1 can be purified by several cycles of autonomous replication in DM-1 cells (Drosophila Melanogaster) taking advantage of the fact that RNA-1 behaves as an autonomous replicon in transfected cells [18].

Detailed Description of the Construction of Recombinant Baculovirus Carrying the Wild Type or Modified Capsomer Gene FHV was grown in DM-1 cells and purified in sucrose and CsCl gradients as described in [19]. The genomic RNA was extracted from the purified virions by treatment with proteinase K and by phenol-chloroform extraction. A single stranded cDNA was made with reverse transcriptase using 20 bases long oligonucleotides complementary to the 3' end sequence [12] (see FIG. 2). A double stranded cDNA was made with standard PCR techniques [20] amplifying the single stranded cDNA using a 20 bases long oligonucleotide, complementary to the 5'-end of the RNA-2, together with the first primer. Both primers carried extra bases coding for selected restriction enzyme sites (Bam-HI site for the 5'-end and Xba-I site for the 3'-end). After the PCR amplification, the double stranded DNA was gel-purified and ligated to pUC18 (Sma I site). For the in vitro transcription of RNA-2 the corresponding cDNA was inserted into the plasmid pBluescript SKII (Stratagene) under the control of phage T7 polymerase. Examples of the above mentioned modifications of FHV RNA-2 are shown in Table 1.

TABLE 1

| Position | Restriction Sites | Comments |
|---|---|---|
| L1 | Kpn I (after mutagenesis) | a) Aminoacids 205 to 209 (ATDPA) deleted from the original sequence.<br>b) Val 204 mutagenized to Gly (GTT to GGT) to create kpn 1 site:<br>$G_{204}$ $T_{205}$<br>GGT ACC<br>CCA TGG<br>c) After oligo insertion, GT duplicates |
| L2 | Pst I (after mutagenesis) | a) Aminoacids 270 to 273 (GSTG) deleted from the original sequence.<br>b) Mutagenesis of the codon usage in $L_{269}$ (CAG to CTG) and $Q_{274}$ (CAA to CAG) to generate Pst I site:<br>$L_{169}$ $Q_{274}$<br>CTG CAG<br>GAC GTC<br>c) After oligo insertion, LQ duplicates. |

TABLE 1-continued

| Position | Restriction Sites | Comments |
|---|---|---|
| L3 | Nhe I<br>Spe I<br>(original) | a) Aminoacids 128 to 134 (VPAGTFP) deleted after doble digestion with Nhe I-Spe I:<br>$A_{126}$ $S_{127}$      $T_{135}$ S136<br><br>NheI  GCT  AGC  Spe I  ACT  AGT<br>        CGA  TCG         TGA  TCA<br>b) $S_{127}$ and $T_{135}$ are regenerated after oligo insertion. There are no duplications of aa. |
| I3 | Bsu36 I<br>(original) | a) There is no loss of aa in the original sequence.<br>b) Oligo insertion duplicates aa $P_{304}$ and $E_{305}$<br>$P_{304}$ $E_{305}$  G<br><br>CCT  GAG  G<br>GGA  CTC  C |
| I2 | BamH I<br>(after mutagenesis) | a) Aminoacids 154 and 155 (TT) are deleted after mutagenesis.<br>b) Change of codon usage in $S_{156}$ (TCA to TCC) to generate BamH I site:<br>$G_{153}$ $S_{156}$<br><br>GGA  TCC<br>CCT  AGG<br>c) GS duplicates after oligo insertion. |
| I1 | Bsu36 I<br>(after mutagenesis) | a) Mutagenesis of $G_{108}$ and $Q_{109}$ to generate Bsu36 I site:<br>$G_{108}$ $Q_{109}$<br>GGA  CAG<br><br>to:  $P_{108}$ $E_{109}$<br>      CCT  GAG  G (of $D_{110}$) |

The cDNA of RNA-2 was also inserted into the vector pVL-1393 (Invitrogene) (Bam-HI/Xba-I sites). In this vector the gene is placed under the control of the polyhedrin promotor and flanked by sequences of the *Autographa californica* Nuclear Polyhedrosis Virus (AcNPV) which allow in vivo production of recombinant virus after cotransfection with AcNPV genomic DNA.

Introduction of Foreign Sequences in the cDNA of RNA-2

Figure 7:
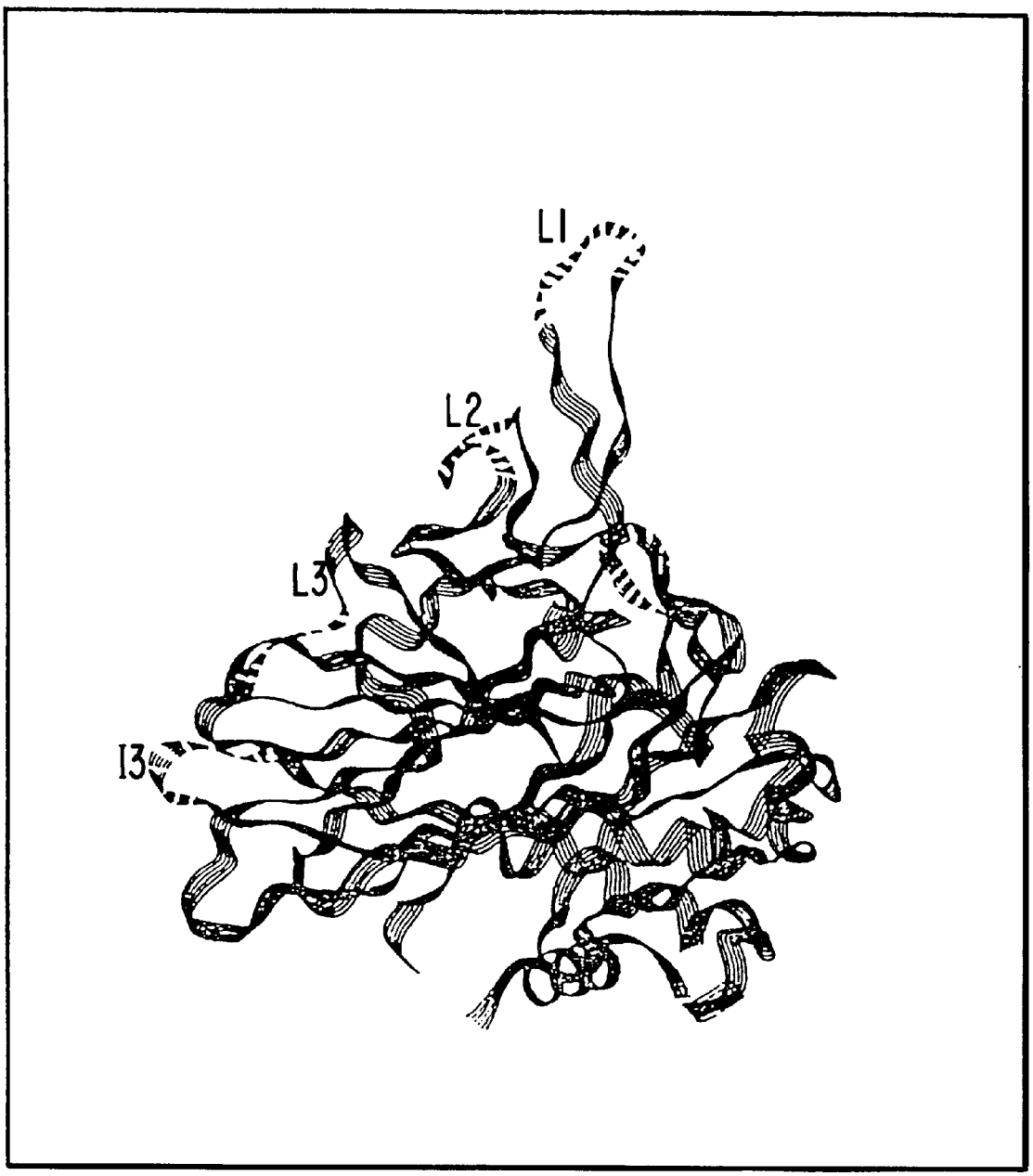
FIG. 7 depicts a stereo diagram of the FHV RNA-2 protein showing the positions in which HIV-1 specific sequences are inserted.

Small insertions/deletions in the sequences of RNA-2 were carried out by the PCR technique [20]. The epitope specific sequences were inserted into one or more of the selected sites either using restriction enzyme sites (when available) or by the PCR technique. The stereo diagram of the FHV capsid protein precursor in FIG. 7 shows the sites where the specific HIV-1 sequences "IGPGRAF" (SEQ ID NO:10) were inserted. Those amino acids were inserted into the positions L1, L2, L3, and I2, whereas the aminoacids "IGPGRAFE" (SEQ ID NO:19) were inserted into position I3. In all positions, except in position I3, certain amino acids were deleted: In position L1 amino acids 205–209 were deleted and aa 204 was mutated to create Kpn I site; in position L2 amino acids 270–273 were deleted and aa 269 and 274 were mutated to create Pst I site; in position L3 amino acids 128–134 were deleted after digestion with Nhe I-Spe I. In position I2 amino acids 154–155 were deleted. See Table 1.

Examples of the insertion of foreign sequences into the recombinant FHV capsomer are listed in Table 2.

TABLE 2

Examples of foreign sequences included in FHV recombinant capsomer

| Sequences | Sites | Amino acids sequence and their characteristics | Expressed in |
|---|---|---|---|
| HBV-PreS1 | I3 | (SEQ ID NO:4) MGTNLSVPNPPAFGANST--NPDWDFNPGGMQWNSTAL<br>Tcell epitope.<br>Receptor binding site. | E. coli |
| HBV-PreS2 | I3 | (SEQ ID NO:5) MQWNSTALDPRVRGL<br>B cell epitope | E. coli |
| HBV-S | L1,L2,L3<br>I2,I3 | (SEQ ID NO:6) CTTPAQGNSMFPSCCCTKPTDGNC<br>B cell epitope | E. coli<br>Baculovirus |
| HCV-core | L1,L2,L3<br>I2,I3 | 1. (SEQ ID NO:7) TNPKPQRKTKRNTNRRPQD<br>2. (SEQ ID NO:8) VKFPGGGQIVGGVYLLPRR<br>B cell epitopes. | E. coli<br>Baculovirus |
| HIV-1 gp120 | L1,L2,L3<br>I2,I3 | (SEQ ID NO:9) IQRGPGRAF  (IIIB)<br>(SEQ ID NO:10) IGPGRAF    (MN)<br>(SEQ ID NO:11) FGPGQAL    (Mal)<br>(SEQ ID NO:12) IGPGRTL    (NY5)<br>(SEQ ID NO:13) KGPGRVI    (RF)<br>(SEQ ID NO:14) IGLGQAL    (Z2)<br>V3 loop.B cell epitope.<br>Neutralyzing epitope | E. coli<br>Baculovirus |
| HIV-1 gp120 | L1,L2,L3<br>I2,I3 | 1. (SEQ ID NO:15) GKAMYAPPI<br>2. (SEQ ID NO:16) NMWQE(K)VGKA<br>(C4).B cell epitope.<br>Neutralyzing epitope | E. coli<br>Bacufovirus |
| HIV-1 gp41 | L1,L2,L3<br>I2,I3 | (SEQ ID NO:17) ELDKWAS<br>B cell epitope<br>Neutralyzing epitope | E. coli<br>Baculovirus |
| HIV-1 gp41 | L1,L2 L3<br>I2,I3 | (SEQ ID NO:18) IEEEGGERDRDR<br>B cell epitope<br>Neutralyzing epitope | E. coli<br>Baculovirus |

Production of Recombinant Baculovirus Carrying the RNA-2 Gene

The cDNA of RNA-2 (wild-type or after genetic manipulation) was inserted into the transfer vector pVL-1393 under a polyhedrin promotor (sites Bam HI and XbaI of the polylinker). This pUC9 based vector carries a segment of AcNPV in the sequence flanking its polylinker and allows the transfer of the foreign gene to a baculovirus genome after in vivo recombination (see FIG. 8). Insect cells (Spodoptera Frugiperda SF-21 cells) were co-transfected (LIPOFECTIN-cationic liposomes) with linear genomic DNA (non-viable) of AcNPV (BACULOGOLD—*Autographa Californica* Nuclear Polyhedrosis Virus from PharMingen) and with the transfer vector carrying the FHV gene. After 4 days the virus progeny was harvested and titered. Thereafter, several recombinant viruses were plaque purified (3 to 4 times from well isolated plaques). These recombinants were denominated AcNPV-FHV. In some cases the VLPs can tolerate the insertion of up to 20 amino acids without alteration of the assembly process. In other cases, where the insertions prevented the formation of VLPs, this could be circumvented by coinfection with both the wild-type and the modified baculovirus. Thereby, mosaic VLPs were generated carrying both types of capsomer structures.

Production and Purification of VLPs From Insect Cells Infected With AcNPV-FHV In order to obtain purified antigens for immunological antigen studies, Sf-21 cells (in suspension or as monolayer) were infected with recombinant baculoviruses at a multiplicity of infection of 10. Two to three days after the infection 0.5% nonidet P-40 and 0.1% Beta Mercaptoethanol (2-ME) were added to the medium. After 15 minutes on ice, the cell debris were removed by centrifugation for 10 minutes at 12000 g. The VLPs in the supernatant were pelleted through a 30 wt/wt % sucrose cushion (50 mM HEPES, 0.1% 2-ME) at 40.000 rpm in an SW41 rotor for 3 hours at 4 C. The pellet was resuspended in 50 mM HEPES, 0.1% 2-ME and laid on a 10 ml 5–20 wt/wt % continuous sucrose gradient in the same buffer. The particles were sedimented in an SW41 rotor at 40.000 rpm for 1 hour at 11 C. The fractions of the gradient were collected from the bottom and aliquots of each fraction were run on a 10% SDS poyacrylamid gel in order to localize the particle peak. The fractions containing the VLPs were pooled, pelleted by centrifugation and resuspended in the same buffer. The protein content of these preparations was determined by Micro BCA Protein Assay Reagent (Pierce).

Recovery of Modified FHV Containing Exogenous Sequences

Live, recombinant FHV viruses can be recovered when the heterologous amino acid sequences which are inserted into the capsomer do not alter the virion assembly process. The recovery was carried out by co-transfection of DM-1 cells with in vitro made transcripts of modified RNA-2 and authentic RNA-1 purified of RNA-2 by multiple transfection passages at the limiting dilution as described by Ball [18].

EXAMPLE 1

Production of VLPs Carrying the HIV-1 (Human Immunodeficiency Virus, Type 1) Specific Sequence IGPGRAF (SEQ ID NO:10)

Several domains of the HIV-1 gp-120 can induce the production of neutralizing antibodies. One of them is the hypervariable region 3 (V-3 loop). This is a linear, immunodominant epitope known as the "Principal Neutralizing Determinant" (PND) [21, 22]. Although the entire domain varies greatly among different isolates, it was recently found that, may be due to conformation restraints, the amino acid sequence on the tip of the loop is well conserved. Sequence data from 245 isolates from the USA showed that the V3 loop sequence "GPGRAF" (SEQ ID NO:20) was present in more than 60% of the isolates [23]. In addition, it was found that animals immunized with peptides containing this sequence produced sera which could neutralize several diverging isolates, although with a low titer [24]. This sequence was inserted into five different positions on the surface of the FHV structure and in some cases in two sites of the same molecule. The positions selected were the outwards directed loops mentioned above (see FHV structure FIG. 1). In one case (position I3) the foreign sequence was introduced directly as an insert in the original sequence of RNA-2. In order to obtain this, the cDNA coding for the FHV capsid protein was digested with Bsu 36I (cuts the DNA at nucleotide 934), and a synthetic oligonucleotide was inserted coding for the HIV-1 specific sequence. As a consequence of this procedure an additional glutamic acid was inserted at the carboxy terminus of the HIV-1 sequence. The structures of all these recombinant proteins are shown in FIG. 7.

Figure 9A:
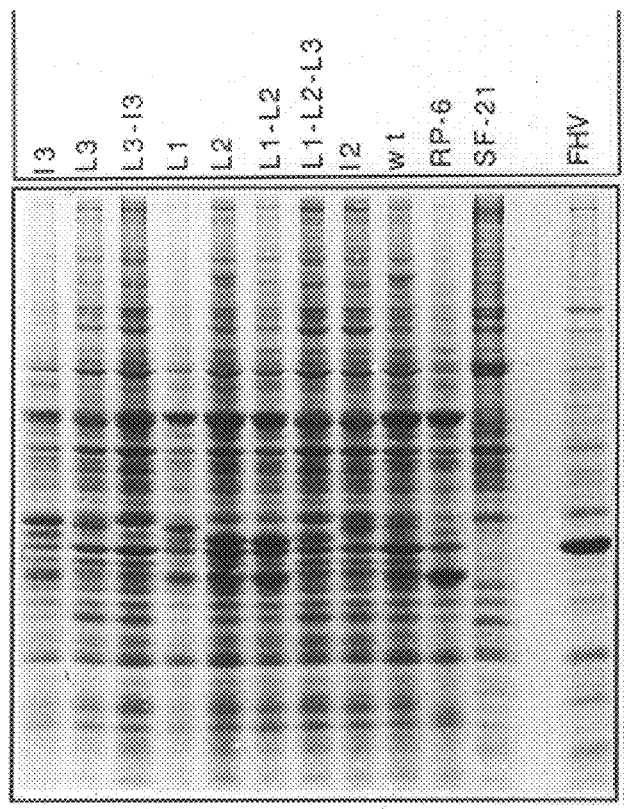
FIGS. 9A and 9B depict expression of the wild-type and the hybrid FHV capsomer.
Figure 9B:
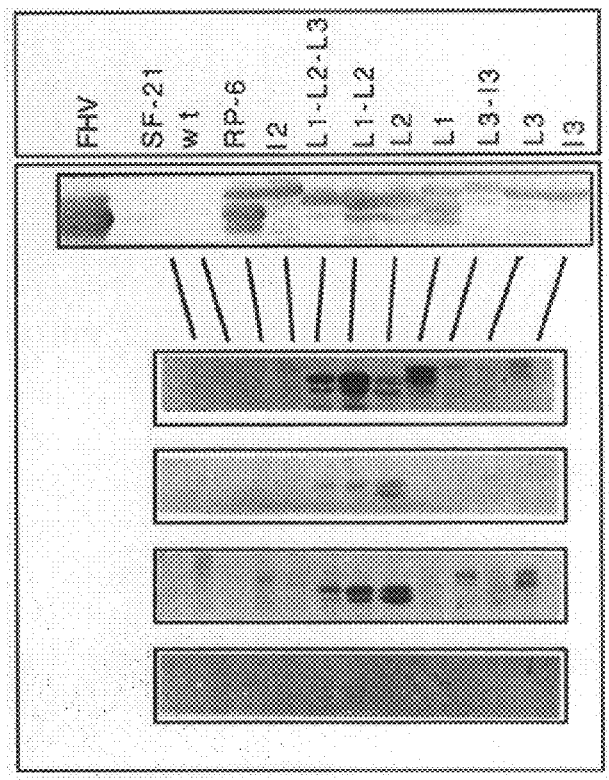

FIGS. 9A and 9B show the proteins induced in Sf-21 cells after infection with the recombinant baculovirus carrying the HIV-1 epitopes in the positions shown in FIG. 7. Cells infected with these recombinants, mock infected cells and cells infected with baculoviruses without inserts were lysed and analyzed in a 10% polyacrylamide gel. Coomassie staining of the gel showed, in the lysates from cells infected with recombinant viruses, the presence of bands with a molecular weight similar to the expected molecular weight for FHV capsomer precursor protein (alpha protein) or its cleavage product. These bands were not present in the case of lysates from cells infected with baculovirus without the insert (AcNPV-RP6). Western blots from similar gels, analyzed with rabbit hyperimmune anti-FHV serum, confirmed the identity of the chimeric proteins. In addition to the alpha precursor, its cleavage product (the mature beta protein) was seen in all cases. This probably indicates that the modified capsomers are still capable of assembling and autocleaving. However, in some cases the percentage of mature protein seemed to be low (e.g. L3; I3; I2), probably indicating that the presence of the insert affects the autocleavage process. When a similar blot was analyzed, either using sera from HIV-1 positive patients or HIV-1 specific human monoclonal antibodies, a quite different pattern of recognition developed. The patients' sera mainly recognized the epitope in the L2 position or in those combinations where this position was used. On the contrary, the monoclonal antibodies strongly recognized the position L1 or combinations derived from that position. Position L3 was also extensively recognized by patients' sera though consistently less than L2. The other positions were barely detectable by these sera. On the other hand, certain human sera detected preferentially proteins carrying the inserts in the positions L3 or I3. This suggests a difference in the specificity of the individual immune response to the same sequence. However, until now the strongest signals were always obtained when the proteins carried the inserts in the positions L1 or L2. Coomassie staining of the gels showed that the differences do not depend upon the amount of induced protein in the insect cells. This confirmed the hypothesis that the antigenicity of the epitope is influenced by its localization. Until now the reason for the differences in the patterns of recognition in different patients could not be explained. Further investigations are now to be carried out to explain these data. For example concerning the origin of the infecting strain, the neutralization titer of the sera, the differences in the idiotypic answers, the difference in the patients' prognosis, etc.

Purification of VLP-V3 From Recombinant, Baculovirus Infected Sf-21 Cells

Figure 10:
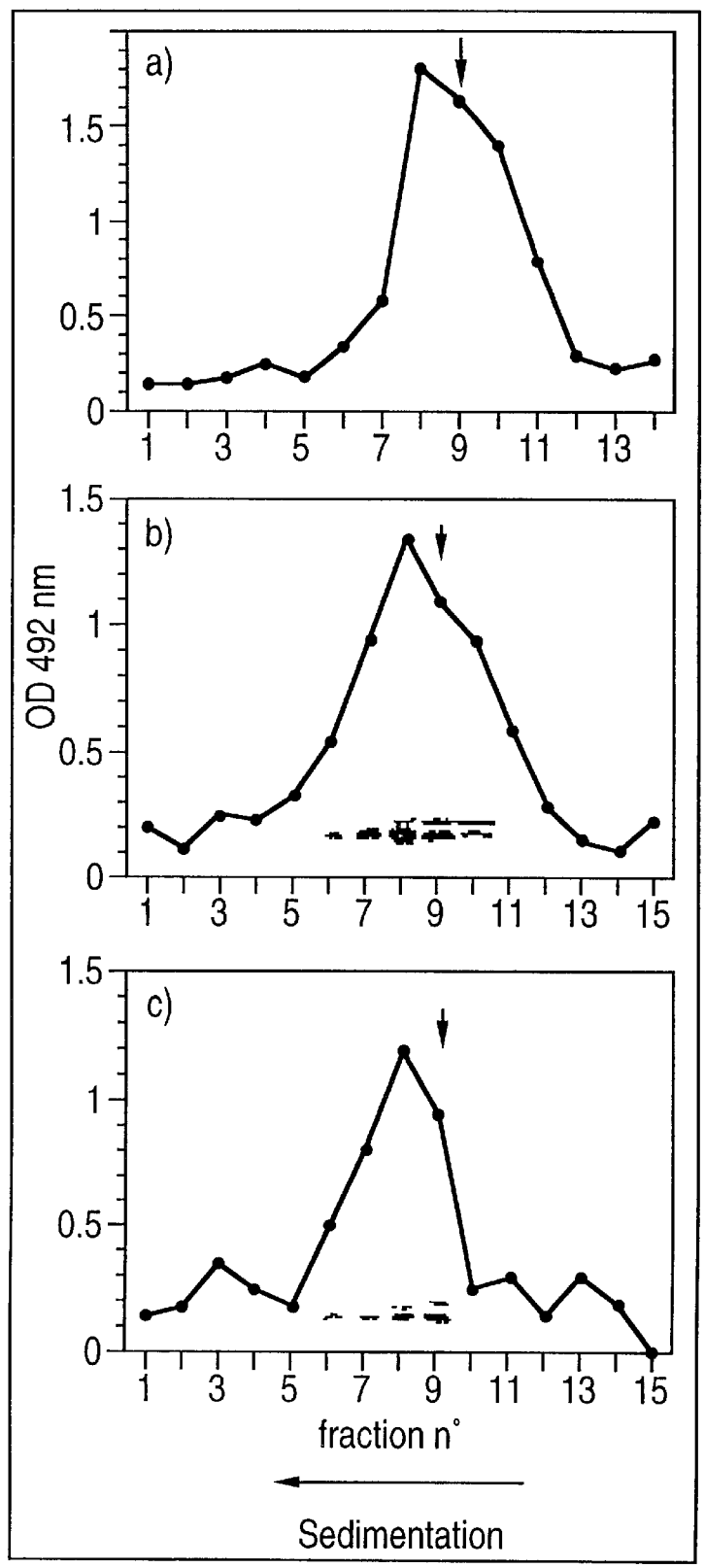
FIGS. 10A–10C depict the sedimentation profile and antigen composition of VLPs produced by three different baculovirus infected SF-21 cells.

FIGS. 10A–10C show the sedimentation profile and the antigen composition of VLPs produced by three different baculovirus: AcNPV-FHV which expresses the unmodified FHV capsid protein; AcNPV-FHV-V3/L1 expressing the same protein yet carrying the HIV-1 epitope in position L1; and AcNPV-FHV-V3/L2 carrying the insert in position L2. See FIG. 7 for details on insert locations. In all cases it was found that the particulate material, obtained as described above, migrated to the same position in the gradient as the FHV particles. The particulate nature of these components was further confirmed by electron microscopy. Aliquots from each peak were run on a polyacrylamide gel and probed with HIV-1 positive serum after transfer to nitrocellulose paper. In all cases the detected proteins migrated to the same position as did the FHV capside protein or its precursor. In the case of wild-type or L1-derived particles the main band corresponded to the mature protein, whereas in L2-derived particles a large quantity of immature protein (alpha protein) was present in addition. However, there seemed to be an increase of mature protein in VLPs when these were compared with the input material prior to the purification. Similar results were also obtained after analysis of the products of those recombinant baculoviruses expressing the FHV capside proteins with the inserts in the other positions described above. The only differences found were the yield of particulate material and the percentage of VLPs carrying immature protein in that material.

The experiments were carried out as follows. Four days after the infection the cells and the medium were processed as previously described and the presence of the particles was analyzed by sucrose density gradient sedimentation (SW50.1 rotor at 45000 rpm for 30 minutes at 20 degrees C.). The fractions were collected from the bottom of the tubes. In order to detect the distribution of the FHV along the gradient, aliquots of each fraction were tested for FHV reactivity by means of an ELISA assay. The distribution of HIV-1 specific reactivity along the gradient was measured through western blotting of samples from the peak fractions. The western blots were probed with HIV-1 positive sera and the resulting bands are shown at the bottom of each graph. FIG. 10A shows the reactivity of AcNPV-FHV-derived particles, FIG. 10B shows particles derived from AcNPV-FHV-V3-L1 and FIG. 10C shows particles derived from AcNPV-FHV-V3-L2. The arrows indicate the migration of FHV run in a parallel gradient.

Immunogenicity of Chimeric VLP-V3 Particles

In order to determine whether the seven HIV-amino acids inserted into the VLP structure were capable of inducing an immune response, three groups of guinea pigs, each consisting of three animals, were immunized with purified VLPs carrying the HIV-1 insert as described in the following. The first group of animals was inoculated with the insert in position L3, the second group with the insert in position I3 and the third group was inoculated with the insert in both positions L3 and I3. All three groups were immunized subcutaneously with 500 microliters PBS containing 50 microgrammes of the respective VLP preparations. For the first immunizations on day 0 the antigens were formulated in complate Freund's adjuvant (CPA). For the boosters on days 14 and 28 the same amount of antigen was formulated in Freund's incomplete adjuvant (IFA). Blood was taken from each animal 35 days after the first inoculation by cardiac puncture. Sera from the immunized animals were tested for specific anti-V3 and anti-FHV antibodies in an ELISA test. The data represent reciprocal dilutions at OD 492. For the anti-FHV titer the ELISA plates were coated with CsCl-purified viruses (200 nanogrammes per well). The titers against the HIV-1 inserts were analyzed on plates coated with recombinant gp120 (ABT-Baculovirus produced, 100 ng per well) as a capture antigen. The data in FIG. 11 show that these preparations had elicited a good antibody response specific for the V3 sequence. As shown by this test, no major differences existed among the various constructs. However, the rest of the positions are yet to be analyzed and an evaluation is to be made of the differences in the affinity shown to the native gp-120 by the immune sera, a parameter known to be associated with their neutralizing capacity.

EXAMPLE 2

Hepatitis C Virus (HCV)

The transfusion induced Hepatitis, which can neither be attributed to Hepatitis A virus nor to Hepatitis B virus (NANBH), belongs to the main group of transfusion transmitted diseases [25]. The cloning and expression of HCV has allowed the development of antibody screening immunoassays for the detection of HCV infections, using as solid phase antigen a fusion polypeptide expressed through recombinant yeast. Initial studies using this protein confirmed that HCV was the predominant agent of NANBH. However, these and subsequent studies demonstrated a series of shortcomings with this serological test due to low sensitivity and specificity. The tests currently used are mostly based on the detection of antibodies against the non-structural proteins NS3–NS4 which, however, do not appear in infected patients until the disease is in an advanced state (4–6 months after the onset of the Hepatitis). Later, it was demonstrated that most immunodominant epitopes are located within the aminoterminal parts of the core protein [25, 26, 27] and that antibodies against these epitopes appear early after the infection. This was shown either by using recombinant HCV-core protein produced in bacteria or baculovirus, or by using synthetic peptides corresponding to these sequences. Moreover, the HCV-core protein is considered as the most significant single antigen for the detection of antibodies in infected patients. Among all positive samples 80–85% are found to be core positive and in most of them this was the only antigen recognized.

Production of FHV-VLPs Carrying an HCV-core Epitope

Figure 12:
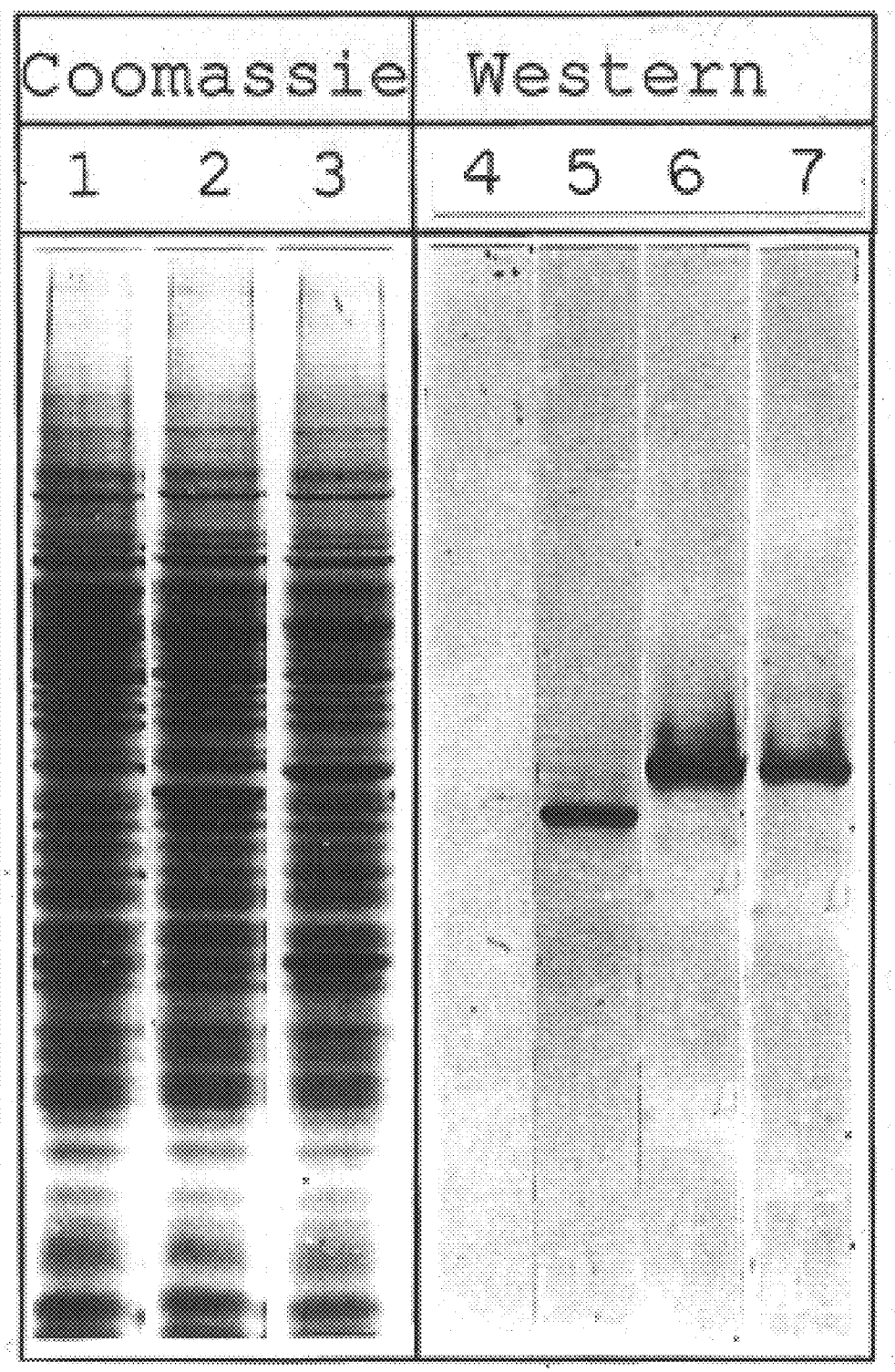
FIG. 12 depicts the expression of hybrid FHV-HCVc proteins through recombinant Baculovirus AcNPV-HCVc.

With reference to these considerations, the epitopes of the HCV core protein were tested in the molecular presentation system of the invention here reported. A 20 amino acids long sequence was selected corresponding to the amino acids 20–40 in the original sequence about which it had already been shown that they were very effective for diagnostic purposes [26]. The 20 amino acids long epitope was inserted in the I3 position on the Bsu-36I site of the RNA-2 gene contained in pVL-1393. The recombinant Baculovirus was produced and purified as described. The resulting recombinant was denominated AcNPV-HCVc. FIG. 12 shows the expression of hybrid FHV-HCV proteins through the recombinant baculovirus AcNPV-HCVc. The chimeric capsomer was produced through the recombinant baculovirus as follows. Sf-21 cells were infected with recombinant baculovirus AcNPC-HCVc (lane 3, 6, and 7), with a baculovirus carrying an unmodified FHV capside protein AcNPV-FHV (lane 2 and 4) and with a polyhedrin-minus baculovirus carrying no insert AcNPV-RP6 (lane 1), respectively. The whole cell extracts were run in a 10% SDS-Page gel. Purified FHV was included as a marker (lane 5). Lanes 1–3 were stained with Coomassie blue. After the running, the proteins in lanes 4–7 were blotted on Nitrocellulose paper. After staining with Poinceau red, paper strips corresponding to each well were cut out and probed with a specific serum. Lanes 4 and 6 were probed with serum from a patient who was core positive in a RIBA-II test. Lanes 5 and 7 were probed with rabbit-anti-FHV serum.

The insect cells were infected with the recombinant virus and four days after the infection the cells were lysed and analyzed on a 10% SDS-PAGE gel. After the running, the gel was stained with Coomassie brilliant blue. The introduction of HCV-sequences apparently had no influence on the protein production. However, all the detected protein migrated with the molecular weight of the precursor (alpha protein). This indicates that the maturation process is somewhat impaired by the sequence alteration. In order to confirm the identity of this protein, the lysates of the infected cells were run on a similar gel, transferred to Nitrocellulose paper and probed with specific antisera. As expected, the protein reacted strongly with the specific rabbit-anti-FHV antiserum (dilution 1:2000) as well as with HCV positive human serum (dilution 1:200).

Figure 13:
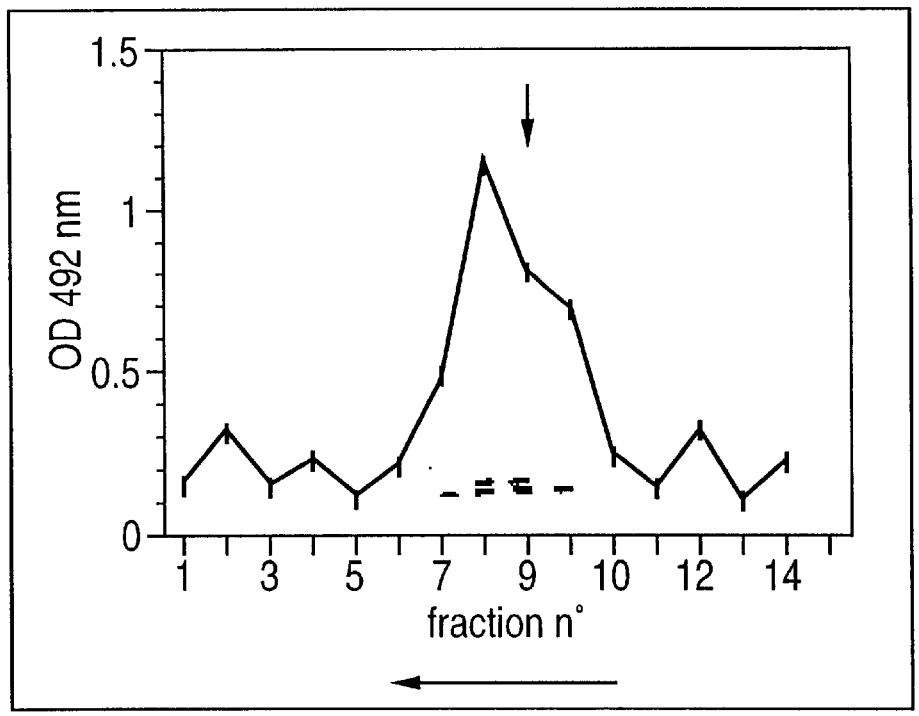
FIG. 13 depicts the profile and FHV reactivity (ELISA test) after a sucrose gradient of VLPs formed by SF-21 infected cells with the recombinant Baculovirus AcNPV-HCV.

FIG. 13 shows the FHV reactivity (measured in an ELISA test) after sucrose sedimentation of VLPs produced by infection of Sf-21 cells with the recombinant baculovirus AcNPV-HCVc. The running conditions were identical to those described in connection with FIG. 10. Aliquots from each peak fraction were western blotted and probed with HCV positive human sera. A photo of the developed Western bands is inserted at the bottom of the graph. The arrow indicates the position of FHV run in a parallel gradient.

As in the case of the particles carrying HIV-1 specific sequences, the particles migrated somewhat slower than the wild-type FHV particles. Western blots of aliquots from the peak reacted with HCV-positive sera. This indicates that the unprocessed protein is not impaired in its ability to autoassemble into a particulate structure.

To asses the capability of the antigen to detect specific antibodies, purified VLPs were used for the ELISA test. Wells of ELISA plates (Nunc) were coated with 100 microliters of purified VLPs diluted in PBS buffer (100 nanogrammes per well). After blocking with PBS containing 5% BSA, 100 microliters of serum dilution were added to each well and the plate was incubated for two hours at room temperature. The bound antibodies were detected by a second incubation with a horse radish peroxidase conjugate of the IgG fraction of goat anti-human immunoglobulin for one hour at room temperature. The enzyme activity was measured using o-phenylendiamine as a substrate. The absorbance of each well was measured at A=490 nanometer. To test the sensitivity of this antigen, 100 sera, known to be core positive in a commercial test (RIBA II-Chiron Corp.), were analyzed. Almost 85% of the samples gave titres higher as 1:1000 which indicates a very good sensitivity when detecting anti-core antibodies. These results demonstrated that these 20 amino acids from the HCV core sequence represent a very reliable antigen for the detection of HCV infections, when introduced in the carrier system of the present invention.

Figure 14:
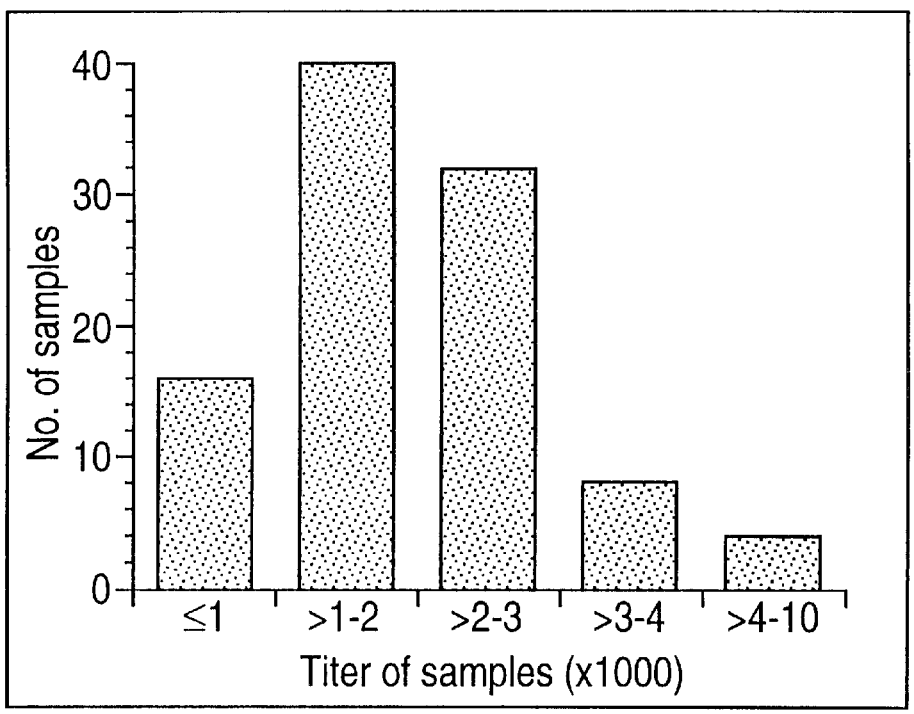
FIG. 14 depicts the distribution of the ELISA titer obtained by VLP based assay among 100 selected HCV core positive sera.
Figure 15:
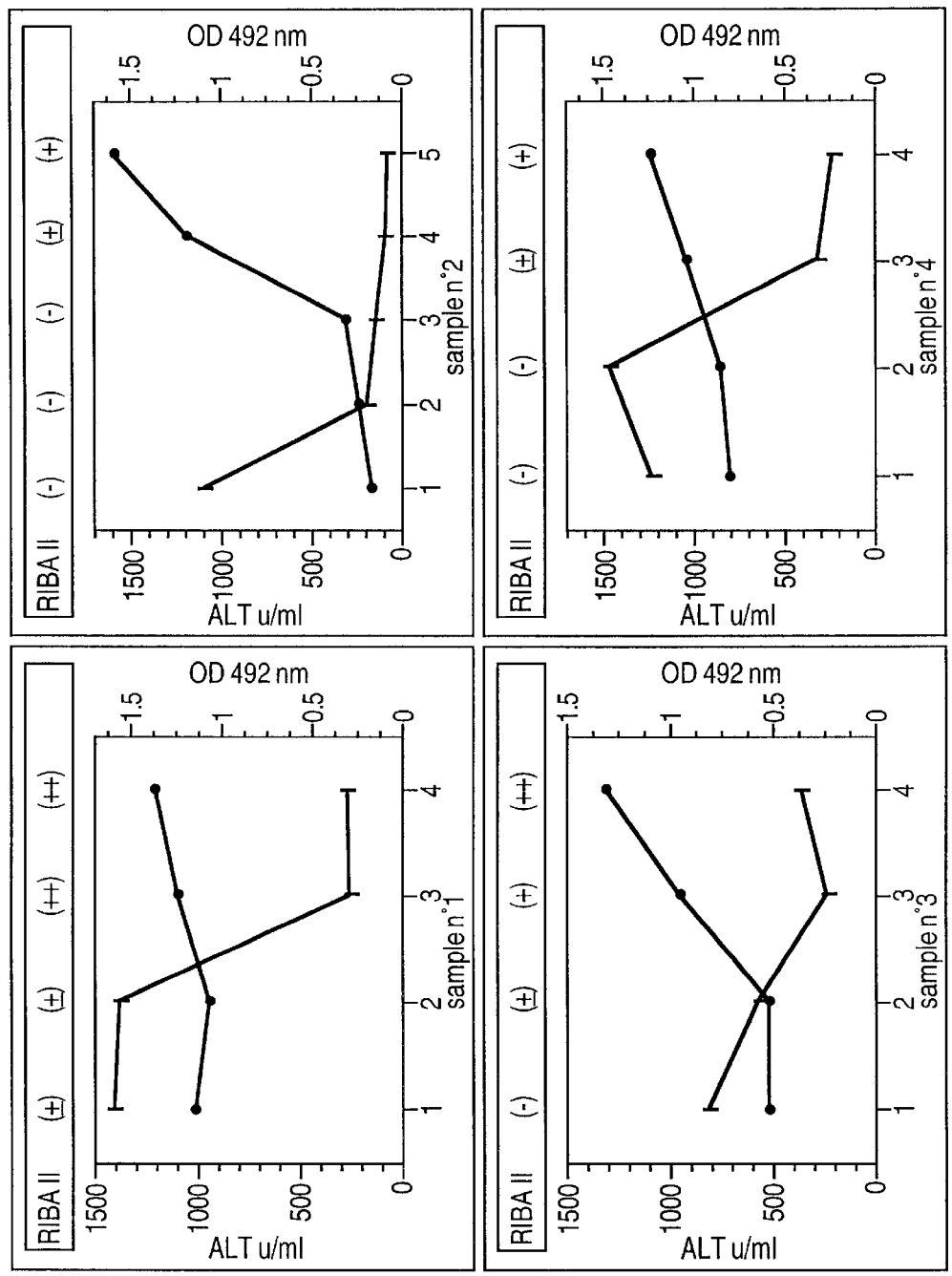
FIGS. 15A–15D depict the detection of HCV specific antibodies in a VLP based ELISA test and its correlation with alanine aminotransferase (ALT) levels and previous currently available test kits (RIBA II) values.

The results are represented in the block diagram in FIG. 14.

Comparison of a VLP-based ELISA Test With Current, Commercially Available Tests

In order to test the sensitivity of this ELISA assay, a collection of serially drawn blood samples from infected patients, encompassing the period of seroconversion, were analyzed for specific HCV core antibodies. At that stage, all patients already have a high level of the specific liver enzyme Alanine aminotransferase (ALT). In four out of 50 patients which were analyzed (see FIGS. 15A–15D) the test subject of this invention showed seroconversion earlier than in the currently available testkits (RIBA II). These results show that the antigen is extremely suitable for detection of contaminated samples in blood banks. The serially drawn blood samples from selected patients, taken for the RIBA-II test before the seroconversion, were analyzed by using plates coated with VLPs carrying an HCV core-specific epitope. The serum dilution was 1:100 for RIBA-II as well as for the ELISA test of the invention here reported. The RIBA-II values are shown in the upper panel. The VLP-based ELISA test values are represented in the diagram as circles, the ALT values as a vertical line.

A Comparison Between Antibody Detection by VLPs, Carrying HCV Core Sequences, and Antibody Detection by the Free HCV Peptide It has been shown that short peptides are very efficient when used as capture antigens for detection of specific antibodies in human as well as animal sera especially in the form of branched peptides [29]. It has also been reported that they react better than the corresponding recombinant antigens [30]. In transfusion induced Hepatitis-C cases it was established that by using peptides as capture antigens, positive sera could be detected as early as one month after the first transfusion. This coincides with the first increase in the specific liver enzymes and would make short amino acid sequences a useful marker for detecting acute specific HCV infections [27]. For this reason it was decided to compare in a dot-blot assay the HCV specific antigens described in the invention at issue with the corresponding free peptides (HCc-2p), with a peptide encompassing the first 20 amino acids of the core (HCc:1p), and with peptides corresponding to other HCV proteins (NS peptides), respectively.

Figure 16:
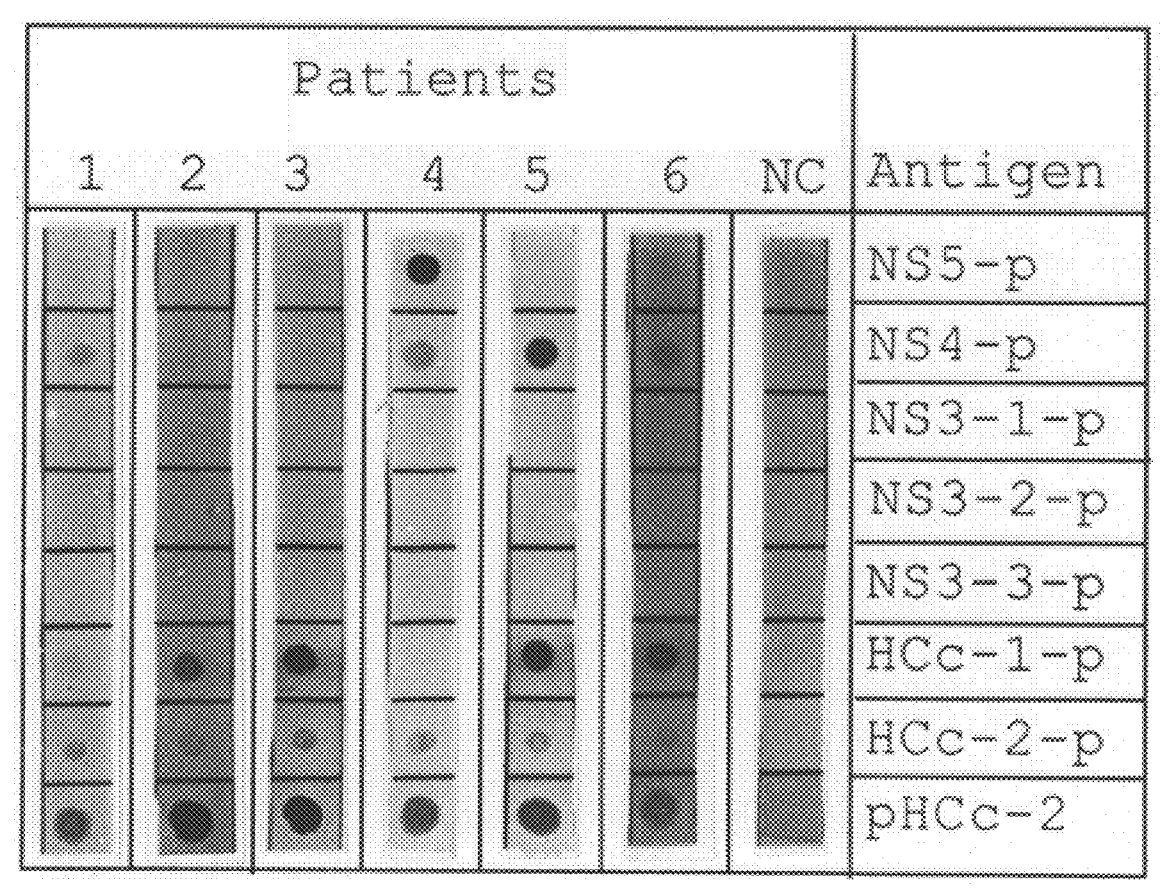

FIG. 16 shows a photograph of these dot-blots which were carried out as follows. Aliquots of 10 microliters of purified VLPs (5 microgrammes per ml), carrying an insert of 20 amino acids from the core of HCV, and solutions containing peptides representing different areas of the HCV genome (100 microgrammes per ml) were blotted on nitrocellulose paper. After blocking with 5% fat free and dry milk, each strip was incubated with a 1:100 dilution of human sera. After washing, each filter was incubated with anti-human antibodies conjugated to horse radish peroxidase (Dako, dilution 1:5000), and finally incubated with diamino benzidine (DAB). Lanes 1–6 show patients' sera. Lane NC shows the negative control serum.

As can be seen, already very low levels of antigen (50 nanogrammes corresponding to 2.5 nanogrammes of the specific HCV peptide) are strong enough, in the form of VLPs, to elicit a good signal with a positive sample. The corresponding free peptide (HCc-2p) gave only a very weak signal although it recognized the same number of positive samples. In this case, the amount of antigen loaded onto the nitrocellulose paper was 400 times higher as in the case of the VLPs, based on a molar ratio. The peptide corresponding to the first 20 amino acids (HCc-1p) gave stronger signals, but failed to detect one positive sample and gave an indeterminate result with another positive sample. Peptides which corresponded to other HCV proteins and which were designed on the basis of published results [31] are far less efficient for detection of HCV positive sera.

We claim:

1. A molecular presentation system utilizing a viral protein carrier comprising a Flock House Virus (FHV) viral protein in which at least one heterologous amino acid sequence is inserted into at least one region of the outwardly directed loops of the Flock House Virus capsid protein.

2. A system according to claim 1, wherein said heterologous amino acid sequence is a epitope.

3. A system according to claim 1, wherein said viral protein is a recombinant protein, or viral particle, and is obtained from the expression of the FHV capsid protein in prokaryotic or eukaryotic cells.

4. A system according to claim 3, wherein said FHV capsid protein is encoded by the modified RNA-2 gene shown in SEQ ID NO:2.

5. A system according to claim 4, wherein said modified RNA-2 gene encodes said outwardly directed loops of the FHV capsid protein designated as loops L1, L2, L3, I1, I2, or I3 in FIG. 1.

6. A system according to claim 5, wherein the regions of the loops selected for the insertion of the heterologous amino acid sequences are selected from the group consisting of the following amino acid sequence regions of the FHV capsid protein of SEQ ID NO:3:

Loop L1 amino acid sequence region 195–219;
Loop L2 amino acid sequence region 263–277;
Loop L3 amino acid sequence region 129–138;
Loop I1 amino acid sequence region 107–110;
Loop I2 amino acid sequence region 152–165; and
Loop I3 amino acid sequence region 304–310.

7. A process for the production of a molecular presentation system utilizing a viral protein carrier comprising
modifying the RNA-2 gene encoding the Flock House Virus capsid protein in at least one of the regions encoding loops L1, L2, L3, I1, I2, or I3 designated in FIG. 1, by at least one modification selected from the group consisting of a deletion, mutagenesis and an insertion in said regions to create at least one enzyme restriction site; and inserting at least one DNA sequence encoding at least one heterologous amino acid sequence into said restriction site.

8. The process for the production of a molecular presentation system utilizing the viral protein carrier according to claim 7, wherein the regions of the loops selected for the insertion of the heterologous amino acid sequences are selected from the group consisting of the following amino acid sequence regions of the FHV capsid protein of SEQ ID NO:3:

Loop L1 amino acid sequence region 195–219;
Loop L2 amino acid sequence region 263–277;
Loop L3 amino acid sequence region 129–138;
Loop I1 amino acid sequence region 107–110;
Loop I2 amino acid sequence region 152–165; and
Loop I3 amino acid sequence region 304–310.

9. A method of inducing an immune response against at least one specific amino acid sequence in a subject comprising administering a Flock House Virus (FHV) viral protein in which at least one heterologous amino acid sequence is inserted into at least one region of the outwardly directed loops of the Flock House Virus capsid protein to said subject.

10. A method of detecting the presence of antibodies to specific amino acid sequences in a sample comprising contacting said sample with a Flock House Virus (FHV) viral protein in which at least one heterologous amino acid sequence is inserted into at least one region of the outwardly directed loops of the Flock House Virus capsid protein; and detecting binding of said FHV viral protein to said antibodies.

* * * * *